(12) United States Patent
Genin et al.

(10) Patent No.: US 11,401,274 B2
(45) Date of Patent: Aug. 2, 2022

(54) [1,2,4]TRIAZOLO DERIVATIVES AS PDE1 INHIBITORS FOR THE TREATMENT OF DIABETES

(71) Applicant: Eli Lilly and Company, Indianapolis, IN (US)

(72) Inventors: Michael James Genin, Danville, IN (US); William Glen Holloway, Brownsburg, IN (US); Cynthia Darshini Jesudason, Indianapolis, IN (US); Qing Shi, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 17 days.

(21) Appl. No.: 16/628,164

(22) PCT Filed: Aug. 3, 2018

(86) PCT No.: PCT/US2018/045081
§ 371 (c)(1),
(2) Date: Jan. 2, 2020

(87) PCT Pub. No.: WO2019/032383
PCT Pub. Date: Feb. 14, 2019

(65) Prior Publication Data
US 2021/0147437 A1    May 20, 2021

Related U.S. Application Data

(60) Provisional application No. 62/543,427, filed on Aug. 10, 2017.

(51) Int. Cl.
*C07D 491/147* (2006.01)
*C07D 487/04* (2006.01)

(52) U.S. Cl.
CPC ....... *C07D 491/147* (2013.01); *C07D 487/04* (2013.01)

(58) Field of Classification Search
CPC ................ C07D 491/147; C07D 487/04
See application file for complete search history.

(56) References Cited

U.S. PATENT DOCUMENTS

| | | |
|---|---|---|
| 6,451,796 B1 | 9/2002 | Kobayashi et al. |
| 8,299,080 B2 | 10/2012 | Okada et al. |
| 9,175,010 B2 | 11/2015 | Branstetter et al. |
| 9,868,741 B2 | 1/2018 | Jesudason |
| 10,138,244 B2 | 11/2018 | Rekhter et al. |

FOREIGN PATENT DOCUMENTS

| | | |
|---|---|---|
| EP | 0040401 B1 | 3/1984 |
| EP | 2103613 B1 | 2/2016 |
| EP | 2615096 B1 | 8/2019 |
| WO | 2008/103357 A1 | 8/2008 |
| WO | 2017/139186 A1 | 8/2017 |

OTHER PUBLICATIONS

Afsar et al., 2015, Int Urol Nephrol, 47:1521-1528.*
Nephrology, 2021, https://www.dukehealth.org/treatments/nephrology?utm_source=google&utm_medium=cpc&cr=kidney_transplant&utm_campaign=TRANSPLANT+-+Kidney+-+Condition+-+NB&keyword=kidney%20disease%20treatment&gclid=Cj0KCQjwm9yJBhDTARIsABKIcGbMOhXr56JtiSC234jrKS9tC7zPp0Da-1dxCTP9JevHulOhYi63BBkaAozeEALw_wcB.*
Al-Salahi, Rashad, "Synthesis of Novel 2-Alkoxy(aralkoxy)-4H-[1,2,4]triazolo[1,5-a]quinazolin-5-ones Starting with Dialkyl-N-Cyanoimidocarbonates," Journal of Heterocyclic Chemistry, 2011, vol. 48, p. 656.

* cited by examiner

*Primary Examiner* — Sun Jae Yoo
(74) *Attorney, Agent, or Firm* — Quarles & Brady LLP

(57) ABSTRACT

The present invention provides a compound of Formula I: wherein X is $CH_2CH_2$, $CH_2CH_2CH_2$, $OCH_2$, or $CH_2O$; and R is ethyl, n-propyl, cyclopropyl, or cyclobutyl; or a pharmaceutically acceptable salt thereof; with the proviso that when X is $CH_2CH_2$, then R is other than cyclopropyl; for use as a human PDE inhibitor.

I

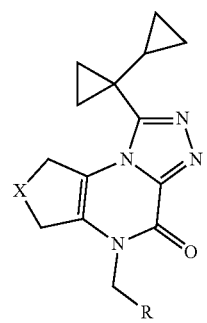

13 Claims, No Drawings

[1,2,4]TRIAZOLO DERIVATIVES AS PDE1 INHIBITORS FOR THE TREATMENT OF DIABETES

The present invention relates to certain human PDE1 inhibitors, to pharmaceutical compositions comprising the compounds, to methods of using the compounds to treat physiological disorders, and to intermediates and processes useful in the synthesis of the compounds.

Phosphodiesterases (PDEs) are enzymes that regulate the cellular levels of cAMP and cGMP by controlling the rate at which these cyclic nucleotides are hydrolyzed. PDE1, a calcium and calmodulin-dependent PDE, is one of at least 11 known PDE families. PDE1 is expressed in many tissues, including the brain, heart, lung, kidney, and smooth muscle. In addition, PDE1 is comprised of a family of three known isoforms, PDE1A, PDE1B, and PDE1C.

Patients suffering from diabetes often develop a form of chronic kidney disease referred to as diabetic kidney disease (or diabetic nephropathy). It has been estimated that diabetic kidney disease may affect as many as 40 percent of diabetic patients. Treatment options for diabetic kidney disease is limited and includes use of medications that lower blood pressure, management of blood glucose levels, diet, and weight, and implementation of regular physical activity. Thus, there is a need for additional treatment choices for patients suffering from chronic kidney disease, particularly diabetic kidney disease.

U.S. Pat. No. 9,175,010 discloses certain thiophene-, furan-, and pyridine-fused azolopyrimidin-5-(6H)-ones which are inhibitors of PDE1, and more particularly, PDE1B, as being useful for treating various physiological disorders, including neurological, cardiovascular, and renal disorders. In addition, European Patent No. 0 040 401 discloses certain substituted triazoloquinoxalin-4-ones possessing anti-hypertensive activity.

The present invention provides certain novel compounds that are inhibitors of human PDE1. In addition, the present invention provides certain novel compounds that are selective inhibitors of human PDE1A, PDE1B, and PDE1C relative to other human PDEs, such as PDE3A, PDE4D, and PDE6AB. Furthermore, the present invention provides certain novel compounds that may have antihypertensive effects and may also improve renal blood flow. In addition, the compounds of the present invention may reduce renal fibrosis.

Accordingly, the present invention provides a compound of Formula I

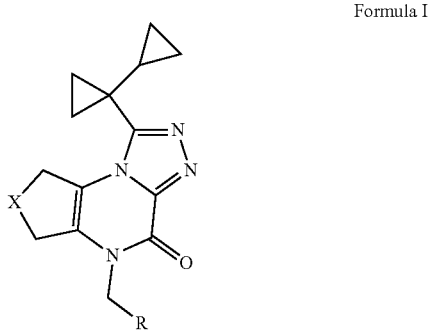

Formula I wherein X is $CH_2CH_2$, $CH_2CH_2CH_2$, $OCH_2$, or $CH_2O$; and R is ethyl, n-propyl, cyclopropyl, or cyclobutyl;

or a pharmaceutically acceptable salt thereof; with the proviso that when X is $CH_2CH_2$, then R is other than cyclopropyl.

The present invention also provides a method of treating chronic kidney disease in a patient, comprising administering to a patient in need of such treatment an effective amount of a compound of Formula I.

The present invention also provides a method of treating diabetic kidney disease in a patient, comprising administering to a patient in need of such treatment an effective amount of a compound of Formula I.

The present invention also provides a method of treating hypertension in a patient, comprising administering to a patient in need of such treatment an effective amount of a compound of Formula I.

In addition, the invention provides a compound of Formula I for use in therapy. The invention further provides a compound of Formula I for use in for the treatment of chronic kidney disease. In addition, the invention provides a compound of Formula I for use in the treatment of diabetic kidney disease. In addition, the invention provides a compound of Formula I for use in the treatment of hypertension. Furthermore, the invention provides the use of a compound of Formula I for the manufacture of a medicament for the treatment of chronic kidney disease. Furthermore, the invention provides the use of a compound of Formula I for the manufacture of a medicament for the treatment of diabetic kidney disease. The invention further provides the use of a compound of Formula I for the manufacture of a medicament for the treatment of hypertension.

The invention further provides a pharmaceutical composition, comprising a compound of Formula I with one or more pharmaceutically acceptable carriers, diluents, or excipients. The invention further provides a process for preparing a pharmaceutical composition, comprising admixing a compound of Formula I with one or more pharmaceutically acceptable carriers, diluents, or excipients. This invention also encompasses novel intermediates and processes for the synthesis of the compound of Formula I.

As used herein, the terms "treating", "treatment", or "to treat" includes prohibiting, restraining, slowing, stopping, or reversing the progression or severity of an existing symptom or disorder.

As used herein, the term "patient" refers to a mammal, such as a dog or a human, with the preferred patient being a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art using known techniques and by observing results obtained under analogous circumstances. In determining the effective amount for a patient, a number of factors are considered by one skilled in the art, including, but not limited to: the patient's size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

Compounds of the present invention are effective at a dosage per day that falls within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are formulated as pharmaceutical compositions administered by any route which makes the compound bioavailable, including oral and parenteral routes. Most preferably, such compositions are for oral administration. Such pharmaceutical compositions and processes for preparing same are well known in the art (See, e.g., Remington: The Science and Practice of Pharmacy, L.V. Allen, Editor, 22$^{nd}$ Edition, Pharmaceutical Press, 2012).

The compounds of Formula I are particularly useful in the treatment methods of the invention, but certain groups, substituents, and compounds are preferred. The following paragraphs describe such preferred groups, substituents, and compounds. It will be understood that these preferences are applicable both to the treatment methods and to the new compounds of the invention.

It is preferred that X is CH$_2$O.
It is preferred that X is OCH$_2$.
It is preferred that R is n-propyl or cyclopropyl.
It is preferred that the compounds of Formula I are in the free base form.
It is more preferred that R is cyclopropyl.
The compounds of Formula Ia (X is OCH$_2$ and R is cyclopropyl) and Formula Ib (X is CH$_2$O and R is cyclopropyl):

Formula Ia

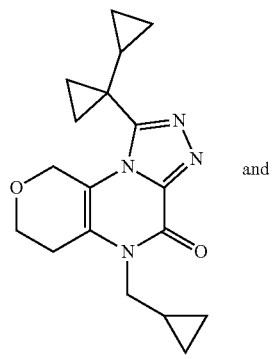

and

Formula Ib

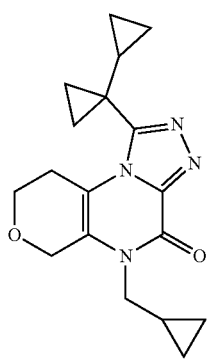

and the pharmaceutically acceptable salts thereof are most preferred with the corresponding free bases being further preferred.

A pharmaceutically acceptable salt of the compound of the invention may be formed, for example, by reaction of an appropriate free base of the compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "ACN" refers to acetonitrile; "AcOH" refers to glacial acetic acid; "CAS #" refers to Chemical Abstracts Service registry number; "c-Bu" refers to cyclobutyl' "c-Pro" refers to cyclopropyl; "d" refers to day or days; "DBU" refers to 1,8-diazabicyclo[5.4.0]undec-7-ene; "Cat. #" refers to catalog number; "DCE" refers to 1,2-dichloroethane; "DCM" refers to dichloromethane or methylene chloride; "DIPEA" refers to N,N-diisopropylethylamine; "DMF" refers to N,N-dimethylformamide; "DMSO" refers to dimethylsulfoxide; "EDC" refers to 1-ethyl-3-(3-dimethylaminopropyl)carbodiimide; "ES/MS" refers to Electrospray Mass Spectrometry; "EtOAc" refers to ethyl acetate; "Et$_2$O" refers to diethyl ether; "EtOH" refers to ethanol; "GCMS" refers to Gas Chromatography Mass Spectometry; "HMDS" refers to hezamethyldisilazane; "HOBT" refers to hydroxybenzotriazole; "hr" refers to hour or hours; "IC$_{50}$" refers to the concentration of an agent that produces 50% of the maximal inhibitory response possible for that agent; "IPA" refers to isopropanol or isopropyl alcohol; "LC-ES/MS" refers to Liquid Chromatography Electrospray Mass Spectrometry; "mol" refers to micromole or micromoles; "min" refers to minute or minutes; "MeOH" refers to methanol or methyl alcohol; "MTBE" refers to methyl-tert-butyl ether; "NiNTA" refers to chromatography with an agarose stationary phase functionalized with nitrilotriacetic acid as chelator; "POCl$_3$" refers to phosphorus oxychloride; "RaNi" refers to Raney nickel; "RT" refers to room temperature; "SD" refers to standard deviation; "SNAr" refers to nucleophilic aromatic substitution; "TEA" refers to triethylamine; "TFA" refers to trifluoroacetic acid; "TFAA" refers to trifluoroacetic anhydride; "THF" refers to tetrahydrofuran; "Tris" refers to 2-amino-2-hydroxymethyl-propane-1,3-diol; "U/ml" refers to units per milliliter; "wt" refers to weight.

The compounds of the present invention may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

Scheme 1

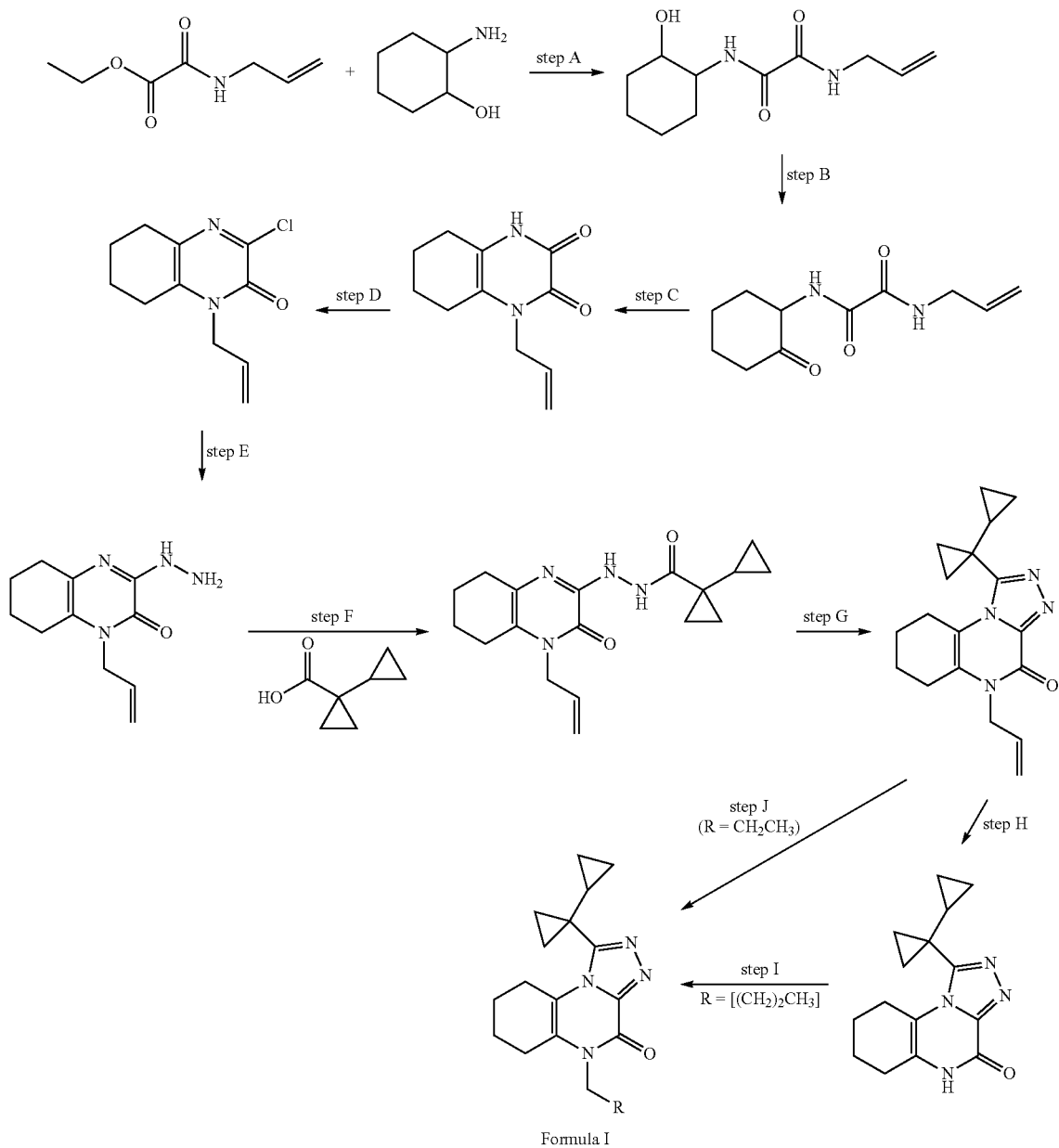

Formula I

Scheme 1 depicts the synthesis of the compounds of Formula I (X=CH$_2$CH$_2$, R=CH$_2$CH$_3$, (CH$_2$)$_2$CH$_3$). In Scheme 1, step A, about 1 equivalent of ethyl-2-(allylamino)-2-oxo-acetate is condensed with about 1.05 equivalents of 2-aminocyclohexanol in the presence of about 1.1 equivalents of a suitable non-nucleophilic organic base such as TEA in a polar organic solvent such as EtOH with heating. The product may be isolated utilizing standard techniques well known in the art, such as filtration. For example, the reaction mixture is cooled and the resulting precipitate is collected by filtration, with subsequent washing with a suitable organic solvent such as EtOAc or Et$_2$O and drying under vacuum, to provide N-allyl-N'-(2-hydroxycyclohexyl)oxamide, the product of Scheme 1, step A, as a mixture of cis and trans isomers of sufficient purity for subsequent use without additional purification.

In Scheme 1, step B, N-allyl-N'-(2-hydroxycyclohexyl) oxamide, the product of Scheme 1, step A, may be oxidized under conditions well known in the art. For example, about 1 equivalent of N-allyl-N'-(2-hydroxycyclohexyl)oxamide is dissolved in a suitable organic solvent mixture, such as THF and DCM, and treated with about 1.1 equivalents Dess-Martin periodinane in the presence of an excess of a suitable inorganic base such as NaHCO$_3$ at 0° C. After warming to ambient temperature, the product may be isolated utilizing standard techniques well known in the art, such as extraction and purification by chromatographic methods. More specifically, the reaction mixture is quenched with aqueous sodium thiosulfate and aqueous saturated NaHCO$_3$. The reaction mixture is extracted with a suitable organic solvent such as DCM, the combined organic extracts are dried over a suitable drying agent such as $Na_2SO_4$, filtered, and concentrated to dryness. The crude product is subjected to purification over silica using a suitable organic solvent mixture, such as hexanes/EtOAc, to provide the product of Scheme 1, step B, N-allyl-N'-(2-oxocyclohexyl) oxamide.

In Scheme 1, step C, about 1 equivalent of N-allyl-N'-(2-oxocyclohexyl)oxamide, the product of Scheme 1, step B, is cyclized under thermal dehydrative conditions in the presence of a mixture of about 1.1 equivalents TFA and 1.1 equivalents TFAA in a suitable acidic solvent such as glacial acetic acid. The product may be isolated utilizing standard techniques well known in the art, such as evaporation and purification by chromatographic methods. More specifically, the reaction mixture is cooled to ambient temperature and evaporated under reduced pressure. The crude product is subjected to purification over silica using a suitable organic solvent mixture, such as MeOH/EtOAc, to provide the product of Scheme 1, step C, 4-allyl-5,6,7,8-tetrahydro-1H-quinoxaline-2,3-dione.

In Scheme 1, step D, about 1 equivalent of the product of Scheme 1, step C, 4-allyl-5,6,7,8-tetrahydro-1H-quinoxaline-2,3-dione, is treated with a suitable chlorinating agent, such as $POCl_3$, and subjected to heating in a suitable organic solvent, such as DCE. The reaction mixture is concentrated under reduced pressure after cooling to ambient temperature to provide the product of Scheme 1, step D, 1-allyl-3-chloro-3,4,5,6,7,8-hexahydroquinoxalin-2-one, suitable for subsequent use without further purification.

In scheme 1, step E, about 1 equivalent of 1-allyl-3-chloro-3,4,5,6,7,8-hexahydroquinoxalin-2-one, the product of Scheme 1, step D, is heated with about 5 equivalents of hydrazine in an appropriate polar organic solvent such as EtOH. The product may be isolated utilizing standard techniques well known in the art, such as extraction. More specifically, the reaction mixture is cooled and concentrated under reduced pressure, partitioned between water and an appropriate organic solvent, such as DCM, and the phases are separated. The organic extract is dried over $Na_2SO_4$, filtered, and concentrated under reduced pressure to obtain 1-allyl-3-hydrazino-5,6,7,8-tetrahydroquinoxalin-2-one, the product of Scheme 1, step E, suitable for subsequent use without additional purification.

In Scheme 1, step F, the product of Scheme 1, step E may be coupled to an acid using a variety of amide coupling techniques well known in the art. For example, about 1 equivalent of 1-allyl-3-hydrazino-5,6,7,8-tetrahydroquinoxalin-2-one, the product of step E, is dissolved in a suitable organic solvent, such as DMF, and treated with about 1.7 equivalents of a suitable amide coupling reagent, such as HATU or TBTU, and 1.7 equivalents of an appropriate carboxylic acid, such as 1-cyclopropylcyclopropanecarboxylic acid (see Eur. J. Org Chem., 2010, pp 3295-3301), in the presence of 3.5-5 equivalents of a suitable non-nucleophilic organic base such as TEA or DIPEA. The product may be isolated utilizing standard techniques well known in the art, such as extraction. More specifically, the reaction mixture is diluted with EtOAc, washed sequentially with saturated aqueous $NaHCO_3$, and saturated aqueous NaCl, dried over $Na_2SO_4$, filtered, and concentrated under reduced pressure to obtain N'-(4-allyl-3-oxo-5,6,7,8-tetrahydroquinoxalin-2-yl)-1-cyclopropyl-cyclopropanecarbohydrazide, the product of Scheme 1, step F, which may be carried forward for use in the next step without additional purification.

In Scheme 1, step G, N'-(4-allyl-3-oxo-5,6,7,8-tetrahydroquinoxalin-2-yl)-1-cyclopropyl-cyclopropanecarbohydrazide, the product of Scheme 1, step F, may be cyclized under thermal or microwave conditions well known in the art. For example, N'-(4-allyl-3-oxo-5,6,7,8-tetrahydroquinoxalin-2-yl)-1-cyclopropyl-cyclopropanecarbohydrazide is dissolved in a suitable organic acid, such as AcOH, and heated in a microwave reactor. The product may be isolated utilizing standard techniques well known in the art, such as chromatographic methods. More specifically, the reaction mixture is concentrated under reduced pressure and the crude product is subjected to chromatography over silica, using an appropriate organic solvent mixture such as hexanes/EtOAc, to obtain 5-allyl-1-(1-cyclopropylcyclopropyl)-6,7,8,9-tetrahydro-[1,2,4]triazolo[4,3-a]quinoxalin-4-one, the product of Scheme 1, step G.

In Scheme 1, step H, 5-allyl-1-(1-cyclopropylcyclopropyl)-6,7,8,9-tetrahydro-[1,2,4]triazolo[4,3-a]quinoxalin-4-one, the product of Scheme 1, step G, may be deallylated under a variety of conditions well known in the art. For example, about 1 equivalent 5-allyl-1-(1-cyclopropylcyclopropyl)-6,7,8,9-tetrahydro-[1,2,4]triazolo[4,3-a]quinoxalin-4-one is dissolved in a suitable degassed organic solvent such as DCM. The solution is treated with about 3 equivalents N,N-dimethylbarbituric acid and about 0.2 equivalents tetrakis(triphenylphosphine)palladium with heating. The product may be isolated utilizing standard techniques well known in the art, such as chromatographic methods. More specifically, the reaction mixture is concentrated under reduced pressure and the resulting residue is subjected to reverse phase column chromatography, using a suitable mixture of buffered water and organic mobile phases, such as ACN containing about 0.1% TFA and water containing about 0.1% TFA, to obtain 1-(1-cyclopropylcyclopropyl)-6,7,8,9-tetrahydro-5H-[1,2,4]triazolo[4,3-a]quinoxalin-4-one, the product of Scheme 1, step H.

In Scheme 1, step I, the product of Scheme 1, step H may be alkylated under a variety of standard alkylation conditions well known in the art. For example, about 1 equivalent of 1-(1-cyclopropylcyclopropyl)-6,7,8,9-tetrahydro-5H-[1,2,4]triazolo[4,3-a]quinoxalin-4-one, the product of step H, is dissolved in a suitable organic solvent, such as DMF, and treated with about 3 equivalents of a suitable strong organic base, such as LHMDS, at or below ambient temperature. The subsequent reaction mixture is treated with a mixture of about 3 equivalents of an appropriate alkylating agent, such as N-butyl iodide. The product may be isolated utilizing standard techniques well known in the art, such as dilution followed by chromatographic methods. More specifically, the reaction mixture is diluted with an appropriate organic solvent such as EtOAc, washed with saturated aqueous NaCl, dried over $Na_2SO_4$, filtered, and concentrated under reduced pressure. The crude product is purified by chromatography over silica, using an appropriate polar organic solvent such as EtOAc, to obtain the compound of Formula I (X=$CH_2CH_2$, R=$(CH_2)_2CH_3$), 5-butyl-1-(1-cyclopropylcyclopropyl)-6,7,8,9-tetrahydro-[1,2,4]triazolo[4,3-a]quinoxalin-4(5H)-one, the product of Scheme 1, step I.

In Scheme 1, step J, the alkene in the product of Scheme 1, step G, may be reduced under a variety of methods well known in the art, such as hydrogenation. For example, about 1 equivalent 5-allyl-1-(1-cyclopropylcyclopropyl)-6,7,8,9-tetrahydro-[1,2,4]triazolo[4,3-a]quinoxalin-4-one, the product of step G, may be subjected to an atmosphere of hydrogen at about 60 psi at ambient temperature in an appropriate polar solvent, such as EtOAc, in the presence of a suitable reducing metal, such as Pd/C or Raney nickel, for about 1 hr. The product may be isolated utilizing standard techniques well known in the art, such as filtration, evaporation, and chromatography. More specifically, the reaction mixture may be filtered and the filtrate concentrated under reduced pressure. The resulting crude product is purified by chromatography over silica, using an appropriate polar organic solvent such as EtOAc, to provide the compound of Formula I (X=CH$_2$CH$_2$, R=CH$_2$CH$_3$), 1-(1-cyclopropylcyclopropyl)-5-propyl-6,7,8,9-tetrahydro-[1,2,4]triazolo[4,3-a]quinoxalin-4(5H)-one, the product of Scheme 1, step J.

3-dione may be combined in excess hydrazine hydrate and the resulting mixture may be heated thermally or subjected to microwave irradiation. The product may be isolated utilizing standard techniques well known in the art, such as dilution and extraction. For example, the reaction mixture is diluted with water and extracted with a suitable organic solvent mixture, such as about 3:1 CHCl$_3$/isopropanol. The extracts are combined, washed with saturated aqueous NaCl,

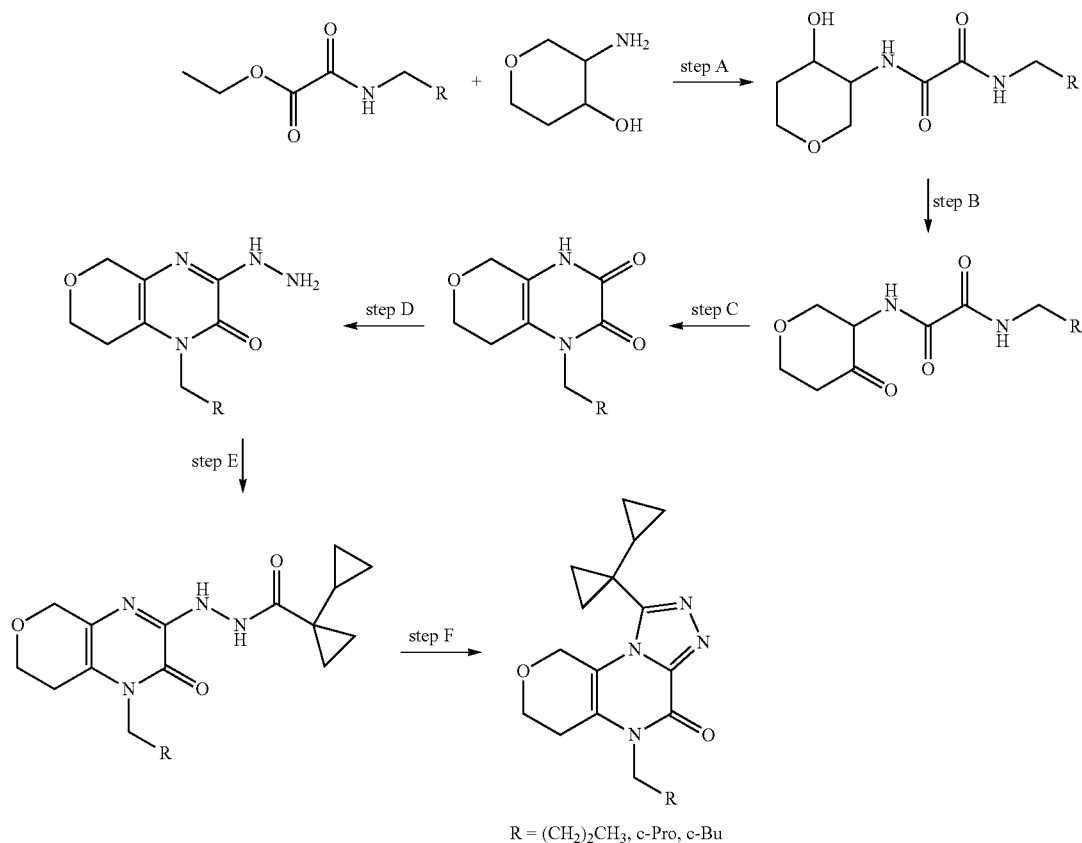

Scheme 2 depicts the synthesis of 5-substituted-1-([1,1'-bi(cyclopropan)]-1-yl-5,6,7,9-tetrahydro-4H-pyrano[4,3-e][1,2,4]triazolo[4,3-a]pyrazin-4-ones (Formula I, X=OCH$_2$, R=(CH$_2$)$_2$CH$_3$, c-Pro, c-Bu). In Scheme 2, step A, about 1 equivalent of 3-aminotetrahydropyran-4-ol is condensed with about 1 equivalent of an appropriately N-substituted ethyl 2-amino-2-oxo-acetate in a polar organic solvent, such as EtOH, at reflux for about 4 hr. The product may be isolated utilizing standard techniques well known in the art, such as filtration. For example, the reaction mixture is cooled to ambient temperature and the resulting solids are collected by filtration, washed with EtOH, and dried under vacuum, to provide N-substituted-N'-(4-hydroxytetrahydropyran-3-yl)oxamide.

In Scheme 2, steps B and C, oxidation of the N-substituted-N'-(4-hydroxytetrahydropyran-3-yl)oxamide, product of Scheme 2, step A, and subsequent cyclization to provide the appropriately substituted 4,5,7,8-tetrahydropyrano[3,4-b]pyrazine-2,3-dione may be performed similarly as described in Scheme 1, steps B and C.

In Scheme 2, step D, about 1 equivalent of the appropriately substituted 4,5,7,8-tetrahydropyrano[3,4-b]pyrazine-2, dried over MgSO4, filtered, and evaporated to dryness under reduced pressure to provide the appropriate 1-substituted-3-hydrazino-7,8-dihydro-5H-pyrano[3,4-b]prazin-2-one.

In Scheme 2, step E, acylation of the appropriate 1-substituted-3-hydrazino-7,8-dihydro-5H-pyrano[3,4-b]prazin-2-one may be accomplished under a variety of amide coupling conditions well known in the art. For example, about 1 equivalent of 1-substituted-3-hydrazino-7,8-dihydro-5H-pyrano[3,4-b]prazin-2-one may be treated with about 1.5 equivalents of 1-cyclopropylcyclopropanecarboxylic acid in the presence of about 1.6 equivalents each of HOBT and EDCI and about 3 equivalents of a non-nucleophilic organic base, such as TEA or DIPEA, in a suitable polar organic solvent, such as DMF or DMSO, at ambient temperature. The product may be isolated utilizing standard techniques well known in the art, such as dilution and extraction. More specifically, the reaction mixture is diluted with water, extracted with a suitable organic solvent, such as EtOAc or DCM, and the extracts are washed sequentially with about 10% aqueous LiCl and saturated aqueous NaCl, dried over Na$_2$SO$_4$, filtered, and concentrated under reduced pressure, to provide the product of Scheme 2, step E, suitable for use without additional purification.

In Scheme 2, step F, cyclization of the product of Scheme 2, step E may be accomplished thermally in a basic, non-nucleophilic solvent such as HMDS containing a non-nucleophilic base such as DIPEA or DBU. For example, about 1 equivalent of the product of Scheme 2, step E may be heated in excess HMDS containing about 0.2-0.8 equivalents DBU at about 120° C. overnight. The product may be isolated utilizing standard techniques well known in the art, such as chromatography. More specifically, the reaction mixture is quenched with MeOH and heated to about 50° C. for 90 min, and the mixture is concentrated under reduced pressure. The resulting residue is purified by flash chromatography on silica gel using a suitable organic solvent mixture, such as EtOAc/DCM and DCM/MeOH, to provide the compound of Formula 1 (X=OCH$_2$, R=(CH$_2$)$_2$CH$_3$, c-Pro, c-Bu), 5-substituted-1-([1,1'-bi(cyclopropan)]-1-yl-5,6,7,9-tetrahydro-4H-pyrano[4,3-e][1,2,4]triazolo[4,3-a]pyrazin-4-one, the product of Scheme 2, step F.

Subsequent oxidation, in Scheme 3, step B, may be performed similarly as described in Scheme 2, step B, to provide the N-substituted-N'-(3-oxotetrahydropyran-4-yl)oxamide, the product of Scheme 3, step B.

In Scheme 3, step C, cyclization of the N-substituted-N'-(3-oxotetrahydropyran-4-yl)oxamide, the product of Scheme 3, step B, to the 4-substituted-1,5,7,8-tetrahydropyrano[3,4-b]pyrazine-2,3-dione, the product of Scheme 3, step C, may be performed similarly as described in Scheme 2, step C.

In Scheme 3, step D, chlorination of the 4-substituted-1,5,7,8-tetrahydropyrano[3,4-b]pyrazine-2,3-dione, the product of Scheme 3, step C, may be performed as described in Scheme 1, step D, to provide the 4-substituted-2-chloro-7,8-dihydro-5H-pyrano[3,4-b]pyrazin-3-one, the product of Scheme 3, step D.

In Scheme 3, step E, conversion of the 4-substituted-2-chloro-7,8-dihydro-5H-pyrano[3,4-b]pyrazin-3-one, the product of Scheme 3, step D, to the 4-substituted-2-hydrazino-7,8-dihydro-5H-pyrano[3,4-b]pyrazin-3-one, the

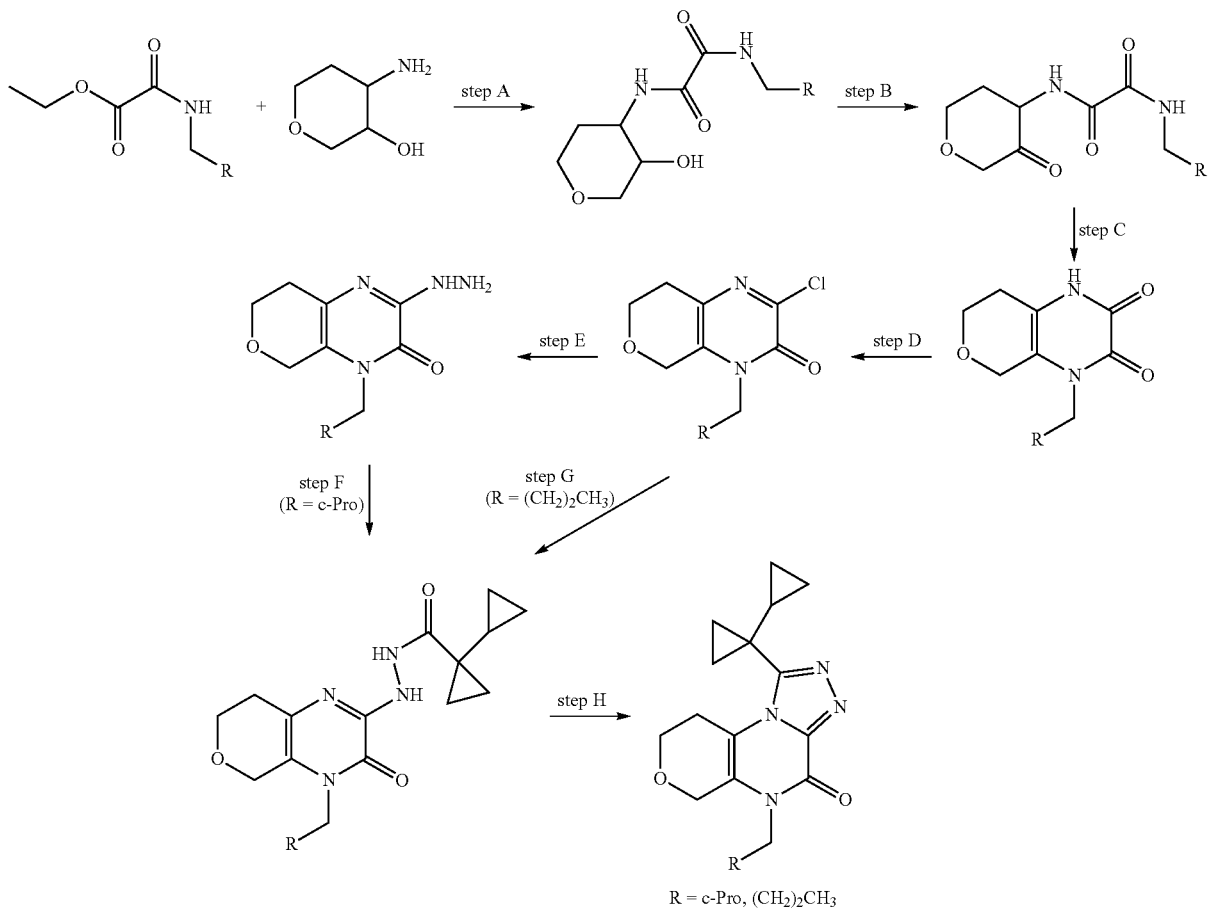

Scheme 3

Scheme 3 depicts the synthesis of 5-substituted-1-([1,1'-bi(cyclopropan)]-1-yl-8,9-dihydro-6H-pyrano[3,4-e][1,2,4]triazoplo[4,3-a]pyrazin-4(5H)-one (Formula I, X=CH$_2$O, R=c-Pro, (CH$_2$)$_2$CH$_3$). Scheme 3, step A, may be performed similarly as described in Scheme 2, step A, to provide the N-substituted-N'-3-hydroxytetrahydropyran-4-yl)oxamide, the product of scheme 3, step A.

product of scheme 3, step E (R=c-Pro), may be accomplished similarly as described in scheme 2, step D.

In Scheme 3, step F, acylation of the 4-substituted-2-hydrazino-7,8-dihydro-5H-pyrano[3,4-b]pyrazin-3-one, the product of scheme 3, step E (R=c-Pro), may be accomplished similarly as described in scheme 2, step E, to provide the N'-(4-substituted-3-oxo-7,8-dihydro-5H-pyrano[3,4-b]

pyrazin-2-yl)-1-cyclopropyl-cyclopropancarbohydrazide, the product of Scheme 3, step F (R═c-Pro).

Alternatively, in Scheme 3, step G, the 4-substituted-2-chloro-7,8-dihydro-5H-pyrano[3,4-b]pyrazin-3-one, the product of Scheme 3, step D (R═(CH₂)₂CH₃), may be heated with 1-cyclopropylcyclopropanecarbohrdazide hydrochloride in an appropriate organic solvent, such as ACN, and subjected to microwave irradiation, to obtain N'-(4-substituted-3-oxo-7,8-dihydro-5H-pyrano[3,4-b]pyrazin-2-yl)-1-cyclopropyl-cyclopropancarbohydrazide, the product of Scheme 3, step G (R═c-Pro). For example, about 1 equivalent of 4-butyl-2-chloro-7,8-dihydro-5Hpyrano[3,4-b]pyrazin-3-one, the product of Scheme 3, step D (R═(CH₂)₂CH₃), is irradiated in the presence of about 0.95 equivalents of 1-cyclopropylcyclopropanecarbohydrazide hydrochloride in ACN at about 100° C. for about 1 hr. The product may be isolated utilizing standard techniques well known in the art, such as extraction. More specifically, the reaction mixture is quenched with water, partially concentrated to about 1%-2 volume under reduced pressure, and the resulting mixture is extracted with an appropriate organic solvent, such as DCM or EtOAc. The organic extracts may be combined, washed with saturated aqueous NaCl, dried over Na₂SO₄, filtered, and concentrated under reduced pressure, to obtain N'-(4-substituted-3-oxo-7,8-dihydro-5H-pyrano[3,4-b]pyrazin-2-yl)-1-cyclopropyl-cyclopropancarbohydrazide, the product of Scheme 3, step G (R═(CH₂)₂CH₃).

In scheme 3, step H, the N'-(4-substituted-3-oxo-7,8-dihydro-5H-pyrano[3,4-b]pyrazin-2-yl)-1-cyclopropyl-cyclopropancarbohydrazide may be cyclized under conditions similar to those described in Scheme 2, step F, to provide 5-substituted-1-([1,1'-bi(cyclopropan)]-1-yl-8,9-dihydro-6H-pyrano[3,4-e][1,2,4]triazoplo[4,3-a]pyrazin-4(5H)-one (Formula I, X═CH₂O, R═c-Pro, (CH₂)₂CH₃), the product of scheme 3, step H.

Scheme 4

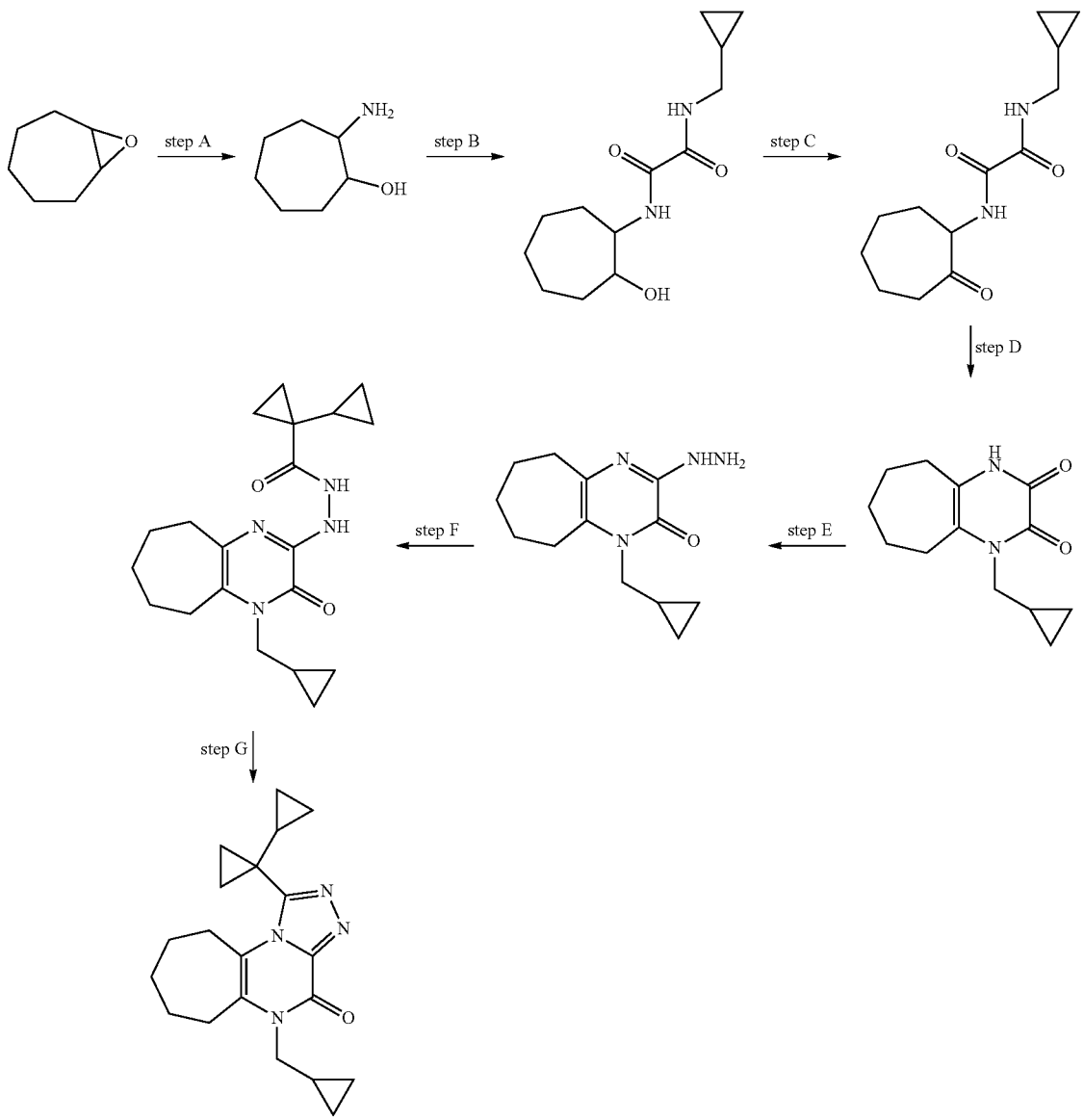

Scheme 4 depicts the synthetic route to 1-([1,1'-bi(cyclopropan)]-1-yl)-5-(cyclopropylmethyl)-5,6,7,8,9,10-hexahydro-4H-cyclohepta[e][1,2,4]triazolo[4,3-a]pyrazin-4-one (Formula 1, X=CH$_2$CH$_2$CH$_2$, R=c-Pro). In Scheme 4, step A, a skilled artisan will recognize that opening the epoxide of 8-oxabicyclo[5.1.0]octane may be accomplished using a variety nucleophiles in a suitable polar organic solvent. For example, about 1 equivalent 8-oxabicyclo[5.1.0]octane may be heated to about 160° C. for about 12-24 hr in a sealed vessel in the presence of NH$_4$OH in a suitable solvent mixture, such as EtOH/THF (2:1). The product may be isolated utilizing standard techniques well known in the art, such as evaporation. More specifically, the reaction mixture may be concentrated under reduced pressure to give 2-aminocycloheptanol, the product of Scheme 4, step A, suitable for use without additional purification.

In Scheme 4, step B, condensation of ethyl 2-(cyclopropylmethylamino)-2-oxoacetate with 2-aminocycloheptanol, the product of Scheme 4, step A, may be accomplished under similar conditions described in Scheme 1, step A, to give N-(cyclopropylmethyl)-N'-(2-hydroxycycloheptyl)oxamide, the product of Scheme 4, step B.

In scheme 4, step C, N-(cyclopropylmethyl)-N'-(2-hydroxycycloheptyl)oxamide, the product of Scheme 4, step B, may be oxidized under similar conditions described in Scheme 1, step B, to give N-(cyclopropylmethyl)-N'-(2-oxocycloheptyl)oxamide, the product of Scheme 4, step C.

In Scheme 4, step D, cyclization of N-(cyclopropylmethyl)-N'-(2-oxocycloheptyl)oxamide, the product of Scheme 4, step C, may be performed as described in Scheme 1, step C, to give 4-(cyclopropylmethyl)-1,5,6,7,8,9-hexahydrocyclohepta[b]pyrazine-2,3-dione, the product of Scheme 4, step D.

In Scheme 4, step E, 4-(cyclopropylmethyl)-1,5,6,7,8,9-hexahydrocyclohepta[b]pyrazine-2,3-dione may be treated with hydrazine under conditions similar to those described in Scheme 2, step D, to provide 4-(cyclopropylmethyl)-2-hydrazino-6,7,8,9-tetrahydro-5H-cyclohepta[b]pyrazin-3-one, the product of Scheme 4, step E.

In Scheme 4, step F, acylation of 4-(cyclopropylmethyl)-2-hydrazino-6,7,8,9-tetrahydro-5H-cyclohepta[b]pyrazin-3-one, the product of Scheme 4, step E, may be accomplished under conditions similar to those described in Scheme 2, step E, to give 1-cyclopropyl-N'-[4-(cyclopropylmethyl)-3-oxo-6,7,8,9-tetrahydro-5H-cyclohepta[b]pyrazin-2-yl]cycloroanecarbohydrazide the product of Scheme 4, step F.

In Scheme 4, step G, 1-cyclopropyl-N'-[4-(cyclopropylmethyl)-3-oxo-6,7,8,9-tetrahydro-5H-cyclohepta[b]pyrazin-2-yl]cyclopropanecarbohydrazide, the product of Scheme 4, step F, may be cyclized under conditions similar to those described in Scheme 2, step F, to provide 1-([1,1'-bi(cyclopropan)]-1-yl)-5-(cyclopropylmethyl)-5,6,7,8,9,10-hexahydro-4H-cyclohepta[e][1,2,4]triazolo[4,3-a]pyrazin-4-one, the product of Scheme 4, step G.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT©HP1100 liquid chromatography system. Electrospray mass spectrometry measurements (acquired in positive and/or negative mode) are performed on a Mass Selective Detector quadrupole mass spectrometer interfaced to the HPi100 HPLC. LC-MS conditions (low pH): column: PHENOMENEX© GEMINI©NX C18 2.1×50 mm 3.0 µm; gradient: 5-100% B in 3 min, then 100% B for 0.75 min; column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA©MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH4HCO3 pH 9; Solvent B: ACN; wavelength: 214 nm.

Preparative reversed phase chromatography is performed on an AGILENT© 1200 LC-ES/MS equipped with a Mass Selective Detector mass spectrometer and a LEAP© autosampler/fraction collector. High pH methods are run on a 75×30 mm PHENOMENEX© GEMINI©-NX, 5µ particle size column with a 10×20 mm guard. Flow rate of 85 mL/min. Eluent is 10 mM ammonium bicarbonate (pH 10) in acetonitrile.

GCMS is performed on an AGILENT© Gas Chromatography system 7890A, equipped with an AGILENT©Mass Selective Detector 5975C and an AGILENT© autosampler 7693, using a Zebron™ gas chromatography capillary column (5% phenylarylene, 95% dimethylpolysiloxane) with dimensions 15 m×0.25 µm×0.25 mm (PHENOMENEX© Cat. #75G-G010-11) from 60-280° C. at 35° C./min and then held at 280° C. for 2 min, with a 90:1 split ratio.

NMR spectra are performed on a Bruker AVIII HD 400 MHz NMR Spectrometer, obtained as CDCl$_3$ or DMSO-d$_6$ solutions reported in ppm, using residual solvent [CDC$_3$, 7.26 ppm; (CD$_3$)$_2$SO, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Preparation 1

N-allyl-N'-(2-hydroxycyclohexyl)oxamide

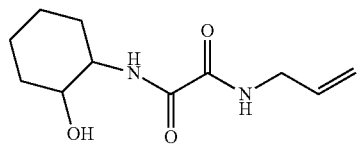 [SMILES: C=CCNC(=O)C(=O)NC1CCCCC1O]

Scheme 1, step A: Combine 2-aminocyclohexanol (7.7 g, 66.8 mmol), ethyl-2-(allylamino)-2-oxo-acetate (10.0 g, 63.6 mmol, Matrix Scientific, CAS #52781-10-9) and TEA (9.8 mL, 70.0 mmol) in EtOH (127.3 mL) and heat the mixture at 80° C. for 4 hr. Cool the mixture to ambient temperature and stir overnight. Isolate the resulting precipitate by vacuum filtration, wash the filter cake with EtOAc, and dry for 4 hr to obtain the title compound (7.2 g, 50% yield) as a white, crystalline solid. Evaporate the filtrate under reduced pressure and sonicate the resulting solid in Et$_2$O. Collect the solid by vacuum filtration, wash the filter cake with Et$_2$O, and dry for 1.5 hr to give an additional lot of the title compound (2.8 g, 19% additional yield) as a white, crystalline solid. The product is a mixture of cis and trans isomers. ES/MS (m/z): 227.0 (M+H).

Preparation 2

N-allyl-N'-(2-oxocyclohexyl)oxamide

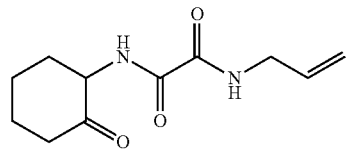 [SMILES: C=CCNC(=O)C(=O)NC1CCCCC1=O]

Scheme 1, step B: Combine N-allyl-N'-(2-hydroxycyclohexyl)oxamide (5.0 g, 22.1 mmol) and NaHCO$_3$ (25.0 g, 297.6 mmol) in a mixture of DCM (110.5 mL) and THF (36.8 mL) and chill the resulting suspension to 0° C. Add Dess-Martin periodinane (10.3 g, 24.3 mmol) to the suspension and allow the mixture to slowly warm to ambient temperature. After stirring overnight at ambient temperature, quench the mixture by the addition of saturated Na$_2$S$_2$O$_3$ (7.0 g in 50 mL of H$_2$O) and saturated aqueous NaHCO$_3$. Stir the biphasic mixture at ambient temperature for 2 hr and separate the layers. Extract the aqueous layer with DCM. Combine the organic extracts, dry over Na$_2$SO$_4$, filter, and concentrate under reduced pressure to give a residue. Purify the residue by flash chromatography over silica gel, eluting with EtOAc:hexanes (1:1), to give the title compound (3.4 g, 69% yield) as an off-white solid. ES/MS (m/z): 225.0 (M+H).

Preparation 3

4-allyl-5,6,7,8-tetrahydro-1H-quinoxaline-2,3-dione

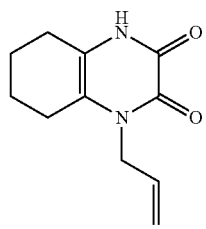

Scheme 1, step C: Add N-allyl-N'-(2-oxocyclohexyl)oxamide (3.4 g, 15.2 mmol) to a mixture of AcOH (15.2 mL, 264.6 mmol), TFA (1.3 mL, 16.7 mmol), and TFAA (3.5 g, 16.7 mmol) and heat the mixture at 100° C. overnight. Cool the mixture to ambient temperature and remove the solvent under reduced pressure to give black oil. Purify the residue by flash chromatography over silica gel, eluting with MeOH:EtOAc (gradient of 0:1 to 1:4), to give the title compound (2.6 g, 83% yield) as a tan solid. ES/MS (m/z): 207.0 (M+H).

Preparation 4

1-allyl-3-chloro-3,4,5,6,7,8-hexahydroquinoxalin-2-one

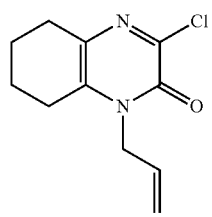

Scheme 1, step D: Add POCl$_3$ (2.0 g, 13.1 mmol) to a solution of 4-allyl-5,6,7,8-tetrahydro-1H-quinoxaline-2,3-dione (2.6 g, 12.5 mmol) dissolved in DCE (62.6 mL) and heat the mixture at 75° C. for 4.5 hr. Add additional POCl$_3$ (1.0 g, 6.3 mmol) to the mixture and continue heating at 75° C. for 3.5 hr. Cool the mixture to ambient temperature and stir overnight. Remove the solvent under reduced pressure and dissolve the resulting residue in toluene. Remove the toluene under reduced pressure to give the title compound (2.81 g, >99% yield) as a dark red oil. ES/MS (m/z): 225.0 (M+H).

Preparation 5

1-allyl-3-hydrazino-5,6,7,8-tetrahydroquinoxalin-2-one

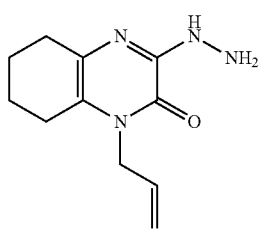 [SMILES: C=CCn1c2c(nc(NN)c1=O)CCCC2]

Scheme 1, step E: Add hydrazine (2.0 g, 62.5 mmol) to a suspension of 1-allyl-3-chloro-3,4,5,6,7,8-hexahydroquinoxalin-2-one (2.8 g, 12.5 mmol) in EtOH (50 mL) and heat the mixture overnight at reflux. Cool the mixture to ambient temperature and remove the solvent under reduced pressure. Partition the resulting residue between H$_2$O and DCM. Separate the organic layer and extract the aqueous layer with DCM. Combine the organic extracts, dry over Na$_2$SO$_4$, filter, and concentrate under reduced pressure to give the title compound (2.6 g, 95% yield) as orange oil. ES/MS (m/z): 221.0 (M+H).

Preparation 6

N'-(4-allyl-3-oxo-5,6,7,8-tetrahydroquinoxalin-2-yl)-1-cyclopropyl-cyclopropanecarbohydrazide

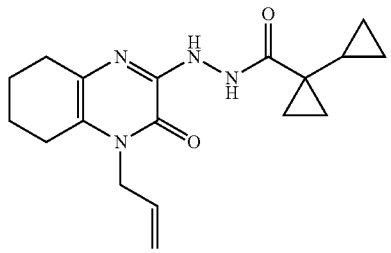 [SMILES: C=CCn1c2c(nc(NNC(=O)C3(C4CC4)CC3)c1=O)CCCC2]

Scheme 1, step F: Add 1-cyclopropylcyclopropanecarboxylic acid (2.3 g, 18.3 mmol), HATU (7.0 g, 18.3 mmol), and DIPEA (6.6 mL, 37.7 mmol) to a solution of 1-allyl-3-hydrazino-5,6,7,8-tetrahydroquinoxalin-2-one (2.4 g, 10.8 mmol) in DMF (40 mL) and stir the mixture overnight at ambient temperature. Dilute the mixture with EtOAc and wash the mixture sequentially with saturated aqueous NaHCO$_3$ and saturated aqueous NaCl. Dry the organic mixture over Na$_2$SO$_4$, filter, and concentrate under reduced pressure to give the title compound (3.5 g, >99% yield) as a brown oil. ES/MS (m/z): 329.2 (M+H).

Preparation 7

5-allyl-1-(1-cyclopropylcyclopropyl)-6,7,8,9-tetrahydro-[1,2,4]triazolo[4,3-a]quinoxalin-4-one

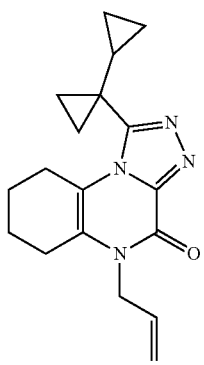 [SMILES: C=CCn1c2c(n3c(C4(C5CC5)CC4)nnc3c1=O)CCCC2]

Scheme 1, step G: Dissolve N'-(4-allyl-3-oxo-5,6,7,8-tetrahydroquinoxalin-2-yl)-1-cyclopropyl-cyclopropanecarbohydrazide (3.5 g, 10.8 mmol) in AcOH (10.0 mL, 174.5 mmol) and heat the solution in a microwave at 130° C. for 3.5 hr. Remove the AcOH under reduced pressure and purify the resulting residue by flash chromatography over silica gel, eluting with EtOAc:hexanes (gradient of 4:1 to 1:0), to give the title compound (1.2 g, 35% yield) as a brown oil. ES/MS (m/z): 311.2 (M+H).

Preparation 8

1-(1-cyclopropylcyclopropyl)-6,7,8,9-tetrahydro-5H-[1,2,4]triazolo[4,3-a]quinoxalin-4-one

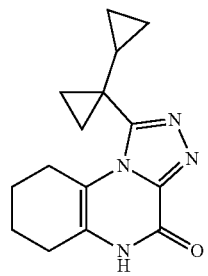 [SMILES: O=c1[nH]c2c(n3c(C4(C5CC5)CC4)nnc13)CCCC2]

Scheme 1, step H: Add N,N-dimethylbarbituric acid (1.3 g, 8.5 mmol) to a solution of 5-allyl-1-(1-cyclopropylcyclopropyl)-6,7,8,9-tetrahydro-[1,2,4]triazolo[4,3-a]quinoxalin-4-one (877.4 mg, 2.8 mmol) in DCM (30 mL) and purge with nitrogen for 10 minutes. Add tetrakis(triphenylphosphine)palladium (653.3 mg, 565.3 µmol) and heat the mixture at 35° C. overnight. Cool the mixture to ambient temperature and remove the solvent under reduced pressure to give a residue. Purify the residue by reverse phase flash chromatography (REDISEP™ Gold C-18, 415 g; gradient: 20-48% of a mixture of 0.1% TFA in ACN in a mixture of 0.1% TFA in H$_2$O over 22.9 min.) to give the title compound (392.7 mg, 51% yield) as a tan solid. ES/MS (m/z): 271.0 (M+H).

Preparation 9a ethyl 2-(cyclopropylmethylamino)-2-oxo-acetate

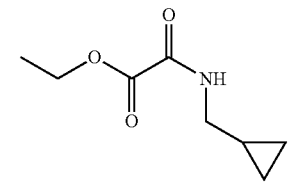

Add TEA (13 mL, 93.3 mmol) to a −10° C. solution of ethyl oxalylchloride (4.1 mL, 37 mmol) in DCM (75 mL). Add cyclopropylmethanamine (3.2 mL, 37 mmol) drop wise and stir the resulting mixture at −10° C. for 3 hr, then warm to RT overnight. Pour the reaction mixture into water, dilute with DCM, and adjust pH to 6-7 with 1 N HCl. Separate the resulting layers and wash the organic layer with saturated aqueous NaCl, dry over Na$_2$SO$_4$, filter, and concentrate under reduced pressure to provide a semi-solid. Dissolve the semi-solid in EtOAc and concentrate under reduced pressure to obtain the title compound (4.3 g, 69% yield). $^1$H NMR (DMSO-d6): δ 0.17-0.13 (m, 2H), 0.39-0.33 (m, 2H), 0.97-0.87 (m, 1H), 1.23 (t, 3H), 2.96 (t, 2H), 4.19 (q, 2H), 8.92 (br s, 1H).

Preparation 9b ethyl 2-(butylamino)-2-oxo-acetate

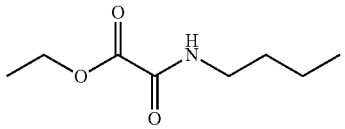

Prepare the compound essentially as described in Preparation 9a, using ethyl oxalylchloride and butylamine, to give the title compound (74% yield). ES/MS (m/z): 174.9 (M+H).

Preparation 10

1-cyclopropylcyclopropanecarbohydrazide hydrochloride

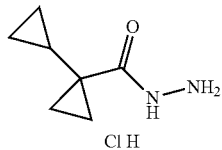

Add a solution of tert-butyl carbazate (10.5 g, 79.4 mmol) dissolved in DMF (100 mL) dropwise to a mixture of 1-cyclopropylcyclopropanecarboxylic acid (10 g, 79.3 mmol), EDCI (16.7 g, 87.1 mmol), HOBT (12 g, 87 mmol), and TEA (12.2 mL, 87.5 mmol) at 0° C. and stir the resulting mixture to RT overnight. Dilute with water, extract with DCM (3×), combine the organic extracts, wash combined organic extracts with 10% aqueous LiCl followed by saturated aqueous NaCl, dry the extracts over $Na_2SO_4$, filter, and concentrate under reduced pressure. Add 4 M solution of HCl in dioxane (40 mL) to the resulting residue and stir at RT overnight. Partially concentrate the reaction mixture under reduced pressure, dilute the concentrated mixture with $Et_2O$, and filter and collect the resulting solid. Dry the solid in vacuum oven for 3 hr to obtain the title compound (11.5 g, 82% yield) as a white solid. ES/MS (m/z): 141.2 (M+H).

Preparation 11

N-(cyclopropylmethyl)-N'-(4-hydroxytetrahydropyran-3-yl)oxamide

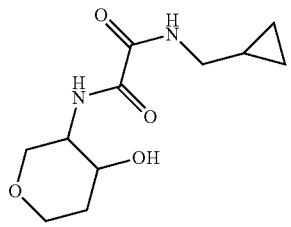 [SMILES: O=C(NCC1CC1)C(=O)NC1COCCC1O]

Scheme 2, step A: Add ethyl 2-(cyclopropylmethyl-amino)-2-oxo-acetate (3.9 g, 17.16 mmol) and triethylamine (6.0 mL, 43 mmol) to a stirred solution of 3-aminotetrahydropyran-4-ol (2.0 g, 17.1 mmol) in EtOH (35 mL). Heat the resulting solution at 80° C. for 4 h. Cool to RT, collect the resulting precipitate by filtration, wash the filter cake with EtOH, and dry the solid under vacuum for 3 d to give the title compound (5.7 g, 93% yield). ES/MS (m/z): 243 (M+H).

Preparation 12

N-(cyclopropylmethyl)-N'-(4-oxotetrahydropyran-3-yl)oxamide

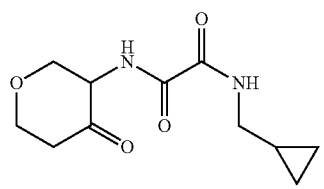 [SMILES: O=C(NCC1CC1)C(=O)NC1COCCC1=O]

Scheme 2, step B: Dissolve N-(cyclopropylmethyl)-N'-(4-hydroxytetrahydropyran-3-yl)oxamide (2.7 g, 11.3 mmol) in DCM (120 mL). Cool the solution to 0° C. in an ice bath and add Dess-Martin periodinane (6.3 g, 14.7 mmol) portion-wise. Warm to RT overnight with stirring. Add additional Dess-Martin periodinane (2.4 g, 5.6 mmol) at RT and stir the reaction for 3 h. Quench the reaction with saturated aqueous $Na_2S_2O_3$ and saturated aqueous $NaHCO_3$ with vigorous stirring for 30 min. Extract the aqueous layer with DCM, combine the extracts, wash with 2N NaOH, dry over anhydrous $MgSO_4$, filter, concentrate under reduced pressure, and dry under vacuum to obtain the title compound (2.1 g, 77% yield). ES/MS (m/z): 241 (M+H).

Preparation 13

1-(cyclopropylmethyl)-4,5,7,8-tetrahydropyrano[3,4-b]pyrazine-2,3-dione

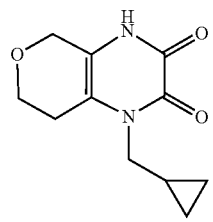 [SMILES: O=c1[nH]c2c(n(CC3CC3)c1=O)CCOC2]

Scheme 2, step C: Dissolve N-(cyclopropylmethyl)-N'-(4-oxotetrahydropyran-3-yl)oxamide (2.1 g, 8.7 mmol) in AcOH (8.7 mL). Add TFA (725 µL, 9.6 mmol) and TFAA (3.7 mL, 26 mmol) and heat to 75° C. for 18 hr. Pour the reaction mixture onto minimal ice and dilute with DCM. Add solid $NaHCO_3$ with stirring until the pH is 5-6. Separate the layers and extract the aqueous layer with DCM. Wash the organic extracts with saturated aqueous NaCl, dry over anhydrous $MgSO_4$, filter, and concentrate under reduced pressure to give the crude title compound (1.5 g, 59% yield). ES/MS (m/z): 223 (M+H).

Preparation 14

1-(cyclopropylmethyl)-3-hydrazino-7,8-dihydro-5H-pyrano[3,4-b]pyrazin-2-one

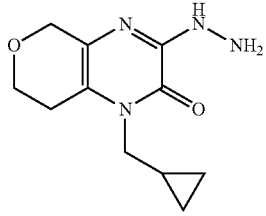 [SMILES: NNc1nc2c(n(CC3CC3)c1=O)CCOC2]

Scheme 2, step D: Combine 1-(cyclopropylmethyl)-4,5,7,8-tetrahydropyrano[3,4-b]pyrazine-2,3-dione (1.5 g, 6.2 mmol) and hydrazine hydrate (10 mL) and irradiate in the microwave at 135° C. for 3 hr. Dilute the reaction with water and extract with 3:1 CHCl₃/IPA. Wash the extracts with saturated aqueous NaCl, dry over anhydrous MgSO₄, filter, and concentrate under reduced pressure to give the crude title compound (475 mg, 27% yield). ES/MS (m/z): 237 (M+H).

Preparation 15

1-cyclopropyl-N'-[1-(cyclopropylmethyl)-2-oxo-7,8-dihydro-5H-pyrano[3,4-b]pyrazin-3-yl]cyclopropanecarbohydrazide

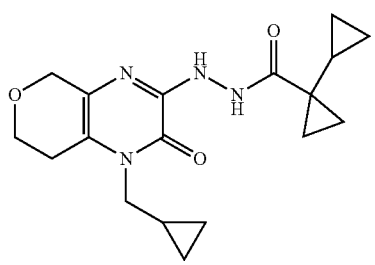 [SMILES: O=C(NNc1nc2c(n(CC3CC3)c1=O)CCOC2)C1(C2CC2)CC1]

Scheme 2, step E: Dissolve 1-(cyclopropylmethyl)-3-hydrazino-7,8-dihydro-5H-pyrano[3,4-b]pyrazin-2-one (475 mg, 1.7 mmol), 1-cyclopropylcyclopropanecarboxylic acid (316 mg, 2.5 mmol), HOBT (368 mg, 2.6 mmol), and EDCI (512 mg, 2.7 mmol) in DMF (4 mL) containing TEA (774 µL, 5.6 mmol). Stir the reaction at RT for 2 hr. Dilute with water and extract with EtOAc. Wash the extracts with 10% aqueous LiCl followed by saturated aqueous NaCl, dry over anhydrous MgSO₄, filter, and concentrate under reduced pressure to give the crude title compound (585 mg, 71% yield). ES/MS (m/z): 345 (M+H).

Preparation 16

N-butyl-N'-(4-hydroxytetrahydropyran-3-yl)oxamide

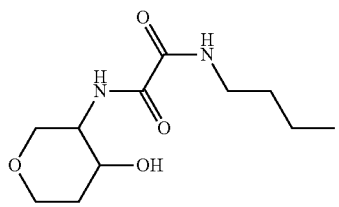 [SMILES: CCCCNC(=O)C(=O)NC1COCCC1O]

Scheme 2, step A: Add ethyl 2-(butylamino)-2-oxo-acetate (2.5 g, 128 mmol) and TEA (4.5 mL, 32 mmol) to 3-aminotetrahydropyran-4-ol (1.5 g, 12.8 mmol) in EtOH (25 mL). Heat the solution at 80° C. for 4 hr. Cool to RT, collect the resulting solids by filtration, wash with EtOH, and dry under vacuum for 4 hr to give the title compound (1.86 g, 59% yield). ES/MS (m/z): 245 (M+H)

Preparation 17

N-butyl-N'-(4-oxotetrahydropyran-3-yl)oxamide

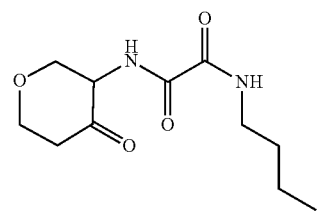

Scheme 2, step B: Dissolve N-butyl-N'-(4-hydroxytetrahydropyran-3-yl)oxamide (1.7 g, 7.2 mmol) in DCM (200 mL). Cool the solution to 0° C. in an ice bath and add Dess-Martin periodinane (3.4 g, 7.9 mmol) portion-wise. Warm to RT and stir mixture over 3 d. Quench with saturated aqueous Na₂S₂O₃ followed by saturated aqueous NaHCO₃ with vigorous stirring for 30 min. Separate the layers and extract the aqueous layer with DCM. Wash the combined organic extracts with saturated aqueous NaCl, dry over anhydrous MgSO₄, filter, concentrate under reduced pressure, and dry under vacuum. Suspend the resulting residue in saturated aqueous Na₂S₂O₃ and saturated aqueous NaHCO₃ overnight. Extract with EtOAc, wash with 1N NaOH followed by saturated aqueous NaCl, dry over anhydrous MgSO₄, filter, concentrate under reduced pressure, and dry under vacuum overnight to give the title compound (1.54 g, 88% yield). ES/MS (m/z): 243 (M+H)

Preparation 18

1-butyl-4,5,7,8-tetrahydropyrano[3,4-b]pyrazine-2,3-dione

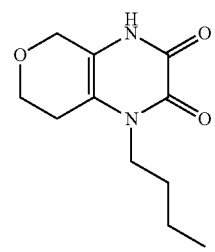 [SMILES: CCCCn1c2c([nH]c(=O)c1=O)COCC2]

Scheme 2, step C: Dissolve N-butyl-N'-(4-oxotetrahydropyran-3-yl)oxamide (1.53 g, 6.32 mmol) in AcOH (6.5 mL), add TFA (530 µL, 7 mmol) and TFAA (1 mL, 7.1 mmol), and heat to 75° C. overnight. Pour the reaction over minimal and dilute with DCM. Add solid NaHCO₃ with stirring to adjust pH 5-6. Separate the layers and extract the aqueous layer with DCM. Wash the combined organic extracts with saturated aqueous NaCl, dry over anhydrous MgSO₄, filter, and Preparation 19

1-butyl-3-hydrazino-7,8-dihydro-5H-pyrano[3,4-b]pyrazin-2-one

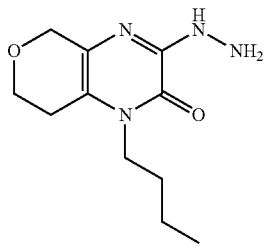 [SMILES: CCCCn1c2c(nc(NN)c1=O)COCC2]

Scheme 2, step D: Combine 1-butyl-4,5,7,8-tetrahydropyrano[3,4-b]pyrazine-2,3-dione (1.3 g, 5.4 mmol) and hydrazine hydrate (10 mL) and irradiate in a microwave at 130° C. for 4 hr. Pour the reaction onto ice and dilute with water. Extract the aqueous layer with 3:1 CHCl$_3$/IPA. Combine the organic layers, wash with saturated aqueous NaCl, dry over anhydrous MgSO$_4$, filter, and concentrate under reduced pressure to obtain the crude title compound (694 mg, 43% yield) which is suitable for use without additional purification. ES/MS (m/z): 239 (M+H).

Preparation 20

N'-(1-butyl-2-oxo-7,8-dihydro-5H-pyrano[3,4-b]pyrazin-3-yl)-1-cyclopropyl-cyclopropanecarbohydrazide

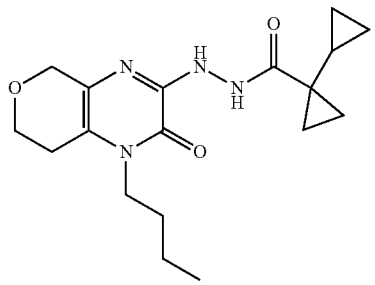 [SMILES: CCCCn1c2c(nc(NNC(=O)C3(C4CC4)CC3)c1=O)COCC2]

Scheme 2, step E: Dissolve 1-butyl-3-hydrazino-7,8-dihydro-5H-pyrano[3,4-b]pyrazin-2-one (694 mg, 2.9 mmol), 1-cyclopropylcyclopropanecarboxylic acid (551 mg, 4.4 mmol), HOBT (643 mg, 4.7 mmol), and EDCI (893 mg, 4.7 mmol) in DMF (6 mL) containing TEA (1.35 mL, 9.7 mmol). Stir at RT overnight. Dilute with water and extract with EtOAc. Wash the combined organic extracts with 10% aqueous LiCl followed by saturated aqueous NaCl, dry over anhydrous MgSO$_4$, filter, and concentrate under reduced pressure to give the crude title compound (832 mg, 66%) suitable for use without additional purification. ES/MS (m/z): 347 (M+H).

Preparation 21

2-aminocycloheptanol

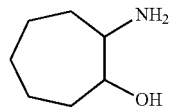

Scheme 4, step A: Add 8-oxabicyclo[5.1.0]octane (3.3 g, 27.9 mmol) to a mixture of 28% aqueous NH$_4$OH (120 mL), EtOH (20 mL), and THF (10 mL). Seal the reaction mixture in an autoclave, purge the reaction mixture with N$_2$, and heat to 160° C. for 14 hr. Cool to RT and concentrate under reduced pressure to obtain the title compound as a brown soft solid (3.2 g, 85% yield). GCMS: (m/z): 129.1 (M+).

Preparation 22 ethyl 2-(cyclobutylmethylamino)-2-oxo-acetate

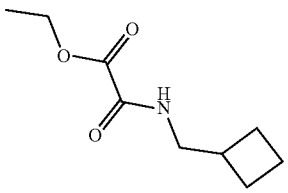

Add a solution of ethyl oxalyl chloride (1.95 mL, 17.4 mmol) in DCM (50 mL) to a mixture of TEA (3.6 mL, 26 mmol) and cylcobutylmethanamine (1.51 g, 17.2 mmol) in DCM (50 mL) at 0° C. over 15 min. Warm the mixture to RT as the ice bath expires. Dilute with water and wash with 0.5 N HCl followed by saturated aqueous NaHCO$_3$. Dry the organic layer over anhydrous MgSO$_4$, filter, and concentrate under reduced pressure to give the title compound (2.45 g, 77% yield). ES/MS (m/z): 186 (M+H).

Preparation 23

N-(cyclobutylmethyl)-N'-(4-hydroxytetrahydropyran-3-yl)oxamide

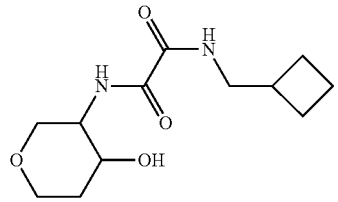 [SMILES: O=C(NCC1CCC1)C(=O)NC1COCCC1O]

Scheme 2, step A: Heat a mixture of 3-aminotetrahydropyran-4-ol (1.55 g, 13.2 mmol), ethyl 2-(cyclobutylmethylamino)-2-oxo-acetate (2.4 g, 13.2 mmol) and TEA (2.0 mL, 14 mmol) in EtOH (25 mL) at 80° C. for 4 hr. Cool to RT and collect the resulting solids by filtration. Dry under vacuum over 3 d to give the title compound (1.7 g, 51% yield). ES/MS (m/z): 257 (M+H).

Preparation 24

N-(cyclobutylmethyl)-N'-(4-oxotetrahydropyran-3-yl)oxamide

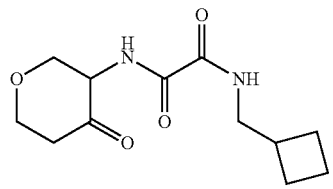 [SMILES: O=C(NCC1CCC1)C(=O)NC1COCCC1=O]

Scheme 2, step B: Dissolve N-(cyclobutylmethyl)-N'-(4-hydroxytetrahydropyran-3-yl)oxamide (1.8 g, 6.9 mmol) in DCM (150 mL) and cool in an ice bath. Add Dess-Martin periodinane (3.8 g, 9.0 mmol) portion wise. Warm to RT overnight as the ice bath expires. Quench the reaction with aqueous saturated $Na_2S_2O_3$ followed by aqueous $NaHCO_3$ with vigorous stirring for 30 min. Extract with DCM, wash organic extracts with 2N NaOH, dry over anhydrous $MgSO_4$, filter, concentrate under reduced pressure, and dry under vacuum to give the title compound (1.81 g, 93% yield). ES/MS (m/z): 255 (M+H).

Preparation 25

1-(cyclobutylmethyl)-4,5,7,8-tetrahydropyrano[3,4-b]pyrazine-2,3-dione

Scheme 2, step C: Dissolve N-(cyclobutylmethyl)-N'-(4-oxotetrahydropyran-3-yl)oxamide (1.8 g, 6.4 mmol), TFA (533 µL, 7 mmol) and TFAA (2.7 mL, 19 mmol) in AcOH (6.4 mL) in a microwave vial. Heat the resulting mixture at 75° C. overnight. Pour onto minimal ice and dilute with DCM. Add solid $NaHCO_3$ with stirring until the pH is 5-6. Separate the layers and extract with dichloromethane. Combine the organic extracts, wash with saturated aqueous NaCl, dry over anhydrous $MgSO_4$, filter, and concentrate under reduced pressure. Dry the resulting dark oil under vacuum and triturate the resulting residue with tert-butyl methyl ether. Collect the resulting sold by filtration, washing with tert-butyl methyl ether, to give crude title compound (1.0 g, 60% yield). ES/MS (m/z): 237 (M+H).

Preparation 26

1-(cyclobutylmethyl)-3-hydrazino-7,8-dihydro-5H-pyrano[3,4-b]pyrazin-2-one

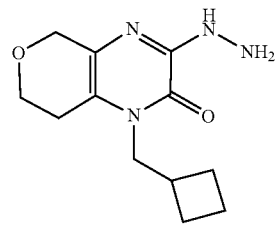 [SMILES: NNc1nc2c(n(CC3CCC3)c1=O)CCOC2]

Scheme 2, step D: Add 1-(cyclobutylmethyl)-4,5,7,8-tetrahydropyrano[3,4-b]pyrazine-2,3-dione (482 mg, 1.8 mmol) to hydrazine hydrate (0.5 mL, 10 mmol) and irradiate at 130° C. in the microwave for 5 hr. Cool to RT and dilute with water; extract the aqueous layer with 3:1 $CHCl_3$/IPA. Wash the combined organic extracts with saturated aqueous NaCl, dry over anhydrous $MgSO_4$, filter, concentrate under reduced pressure, and further dry under vacuum overnight to obtain the crude title compound (275 mg, 51% yield). ES/MS (m/z): 251 (M+H).

Preparation 27

N'-[1-(cyclobutylmethyl)-2-oxo-7,8-dihydro-5H-pyrano[3,4-b]pyrazin-3-yl]-1-cyclopropyl-cyclopropanecarbohydrazide

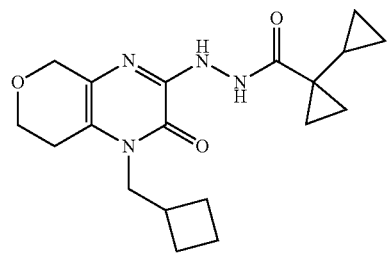 [SMILES: O=C(NNc1nc2c(n(CC3CCC3)c1=O)CCOC2)C1(C2CC2)CC1]

Scheme 2, step E: Dissolve 1-(cyclobutylmethyl)-3-hydrazino-7,8-dihydro-5H-pyrano[3,4-b]pyrazin-2-one (275 mg, 0.9 mmol), 1-cyclopropylcyclopropanecarboxylic acid (178 mg, 1.4 mmol), HOBT (206 mg, 1.5 mmol), EDCI (286 mg, 1.5 mmol) and TEA (433 µL, 3.1 mmol) in DMF (4 mL). Stir the mixture at RT overnight. Dilute with water and extract with EtOAc. Wash the combined organic extracts with 10% aqueous LiCl followed by saturated aqueous NaCl, dry over anhydrous $MgSO_4$, filter, concentrate under reduced pressure, and dry under vacuum overnight to give the crude title compound (334 mg, 85%) sufficient for use without additional purification. ES/MS (m/z): 359 (M+H).

Preparation 28

N-(cyclopropylmethyl)-N'-(3-hydroxytetrahydropyran-4-yl)oxamide

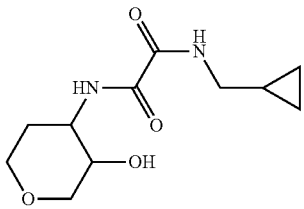 [SMILES: O=C(NCC1CC1)C(=O)NC1CCOCC1O]

Scheme 3, step A: Add TEA (3.9 mL, 28 mmol) to a stirred suspension of 4-aminotetrahydropyran-3-ol (3.0 g, 26 mmol) and ethyl 2-(cyclopropylmethylamino)-2-oxo-acetate (4.4 g, 26 mmol) in EtOH (70 mL) at RT, and heat the resulting reaction mixture at reflux for 2.5 hr. Cool the reaction mixture RT and allow standing overnight. Collect the resulting solids by filtration, suspend in DCM, and wash the mixture with water. Extract the aqueous layer with DCM and wash the combined organic extracts with saturated aqueous NaCl, dry over $Na_2SO_4$, filter, and concentrate under reduced pressure to give the title compound (3.3 g, 53% yield). $^1H$ NMR (DMSO-$d_6$): δ 0.18-0.14 (m, 2H), 0.38-0.34 (m, 2H), 0.98-0.91 (m, 1H), 1.66-1.52 (m, 2H), 2.98-2.91 (m, 3H), 3.27-3.21 (m, 1H), 3.51-3.44 (m, 1H), 3.62-3.54 (m, 1H), 3.75-3.68 (m, 2H), 4.89 (d, 1H), 8.53 (d, 1H), 8.76 (br t, 1H).

Preparation 29

N-(cyclopropylmethyl)-N'-(3-oxotetrahydropyran-4-yl)oxamide

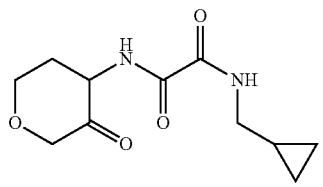 [SMILES: O=C(NCC1CC1)C(=O)NC1CCOCC1=O]

Scheme 3, step B: Stir together N-(cyclopropylmethyl)-N'-(3-hydroxytetrahydropyran-4-yl)oxamide (3.1 g, 12.8 mmol) and $NaHCO_3$ (15.3 g, 173 mmol) in DCM (200 mL) and THF (30 mL) at 0° C. Slowly add Dess-Martin periodinane (6 g, 14 mmol) stir the mixture to RT overnight. Add saturated aqueous $Na_2S_2O_3$ and saturated aqueous $NaHCO_3$, and stir the resulting reaction mixture for 2 hr at RT. Separate the layers, collect the organic layer, and additionally extract the aqueous layer with DCM. Combine the organic extracts, dry over $Na_2SO_4$, and concentrate under reduced pressure. Purify the resulting residue by flash chromatography on silica gel, eluting with hexanes/acetone. Combine the pure chromatography fractions and concentrate under reduced pressure to obtain the title compound (1.9 g, 63% yield). ES/MS (m/z): 241 (M+H).

Preparation 30

4-(cyclopropylmethyl)-1,5,7,8-tetrahydropyrano[3,4-b]pyrazine-2,3-dione

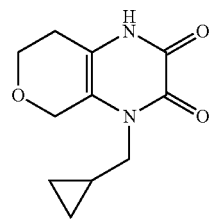 [SMILES: O=c1[nH]c2c(n(CC3CC3)c1=O)COCC2]

Scheme 3, step C: Add TFAA (1.25 ml, 8.9 mmol) and TFA (0.68 mL, 9.0 mmol) to a stirred solution of N-(cyclopropylmethyl)-N'-(3-oxotetrahydropyran-4-yl)oxamide (1.9 g, 8 mmol) in AcOH (8 mL, 139.6 mmol) and heat the resulting homogeneous solution at 100° C. for 15 hr. Dilute the reaction mixture with water and extract with DCM (3×) followed by 3:1 $CHCl_3$/IPA (3×). Combined the organic extracts, wash with saturated aqueous NaCl, dry over $Na_2SO_4$, filter, and concentrate the filtrate under reduced pressure. Purify the resulting residue by flash chromatography on silica gel, eluting with MeOH/DCM. Combine the pure chromatography fractions and concentrate under reduced pressure to obtain the title compound, (948.6 mg, 52.9% yield). ES/MS (m/z): 223 (M+H).

Preparation 31

2-chloro-4-(cyclopropylmethyl)-7,8-dihydro-5H-pyrano[3,4-b]pyrazin-3-one

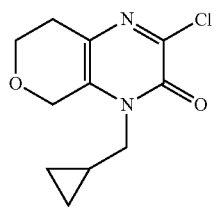 [SMILES: O=c1c(Cl)nc2c(n1CC1CC1)COCC2]

Scheme 3, step D: Stir together 4-(cyclopropylmethyl)-1,5,7,8-tetrahydropyrano[3,4-b]pyrazine-2,3-dione (948.6 mg, 4.3 mmol) and $POCl_3$ (0.48 mL, 5.2 mmol) in DCE (11 mL) at 75° C. for 6 hr, cool to RT, and stir for 3 d. Dilute the reaction mixture with DCM and quench with saturated aqueous $NaHCO_3$ solution with vigorous stirring for 2 hr. Separate the resulting layers, extract the aqueous layer with DCM (2×), combine the organic extracts, and wash with saturated aqueous NaCl, dry over $Na_2SO_4$, filter, and concentrate under reduced pressure to provide the crude title compound (652.3 mg, 44.5% yield) suitable for use without additional purification. ES/MS (m/z): 241 (M+H).

Preparation 32

4-(cyclopropylmethyl)-2-hydrazino-7,8-dihydro-5H-pyrano[3,4-b]pyrazin-3-one

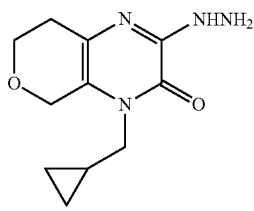 [SMILES: NNc1nc2c(n(CC3CC3)c1=O)COCC2]

Scheme 3, step E: Heat a solution of 2-chloro-4-(cyclopropylmethyl)-7,8-dihydro-5H-pyrano[3,4-b]pyrazin-3-one (652.3 mg, 1.9 mmol) and hydrazine (0.5 mL) in water (0.5 mL) in EtOH (10 mL) at 78° C. overnight. Dilute the reaction mixture with water and extract with DCM (3×). Combine the organic extracts and wash with saturated aqueous NaCl, dry over Na$_2$SO$_4$, and concentrate under reduced pressure to give the title compound (389 mg, 86.8% yield) suitable for use without additional purification. ES/MS (m/z): 241 (M+H).

Preparation 33

1-cyclopropyl-N'-[4-(cyclopropylmethyl)-3-oxo-7,8-dihydro-5H-pyrano[3,4-b]pyrazin-2-yl]cyclopropanecarbohydrazide

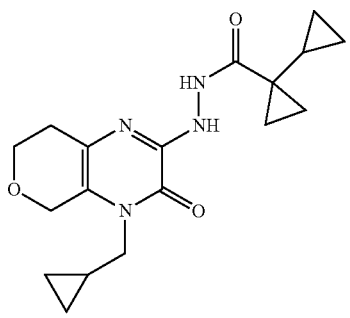 [SMILES: O=C(NNc1nc2c(n(CC3CC3)c1=O)COCC2)C1(C2CC2)CC1]

Scheme 3, step F: Cool a solution of 1-cyclopropylcyclopropanecarboxylic acid (313 mg, 2.4 mmol), EDCI (507 mg, 2.6 mmol), HOBT (365 mg, 2.6 mmol), and TEA (0.8 ml, 6 mmol) in DMF (5.5 ml) to 0° C. in an ice bath and add a solution of 4-(cyclopropylmethyl)-2-hydrazino-7,8-dihydro-5h-pyrano[3,4-b]pyrazin-3-one (389 mg, 1.6 mmol) in DMF (5.5 mL). Warm the resulting mixture to RT with stirring overnight. Dilute the reaction mixture with water and extract with EtOAc (3×). Wash the combined organic extracts with 5% aqueous LiCl solution (2×) followed by saturated aqueous NaCl, and dry the organic extracts over Na$_2$SO$_4$. Concentrate the organic extracts under reduced pressure to obtain the title compound (571.7 mg, 90.7% yield) suitable for use without additional purification. ES/MS (m/z): 345 (M+H).

Preparation 34

N-butyl-N'-(3-hydroxytetrahydropyran-4-yl)oxamide

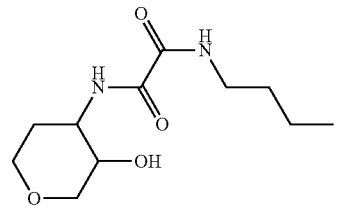 [SMILES: CCCCNC(=O)C(=O)NC1CCOCC1O]

Scheme 3, step A: Add TEA (3.93 mL, 28.2 mmol) to a suspension of 4-aminotetrahydropyran-3-ol (3 g, 25.6 mmol) and ethyl 2-(butylamino)-2-oxo-acetate (4.4 g, 25 mmol) in EtOH (50 mL) at RT. Stir the resulting mixture at reflux for 1 hr and cool to RT. Filter and collect the resulting solid, wash with EtOAc, and air dry for 1 hr to give the crude title compound (4.7 g, 71% yield) suitable for use without additional purification. ES/MS (m/z): 245 (M+H).

Preparation 35

N-butyl-N'-(3-oxotetrahydropyran-4-yl)oxamide

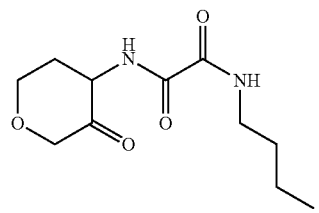 [SMILES: CCCCNC(=O)C(=O)NC1CCOCC1=O]

Scheme 3, step B: Stir N-butyl-N'-(3-hydroxytetrahydropyran-4-yl)oxamide (4.7 g, 19 mmol) and NaHCO$_3$ (5.1 g, 58 mmol) in a mixture of DCM (96 mL) and THF (32 mL) at 0° C. Slowly add Dess-Martin periodinane (10 g, 23.3 mmol) and stir the reaction mixture at RT overnight. Add saturated aqueous Na$_2$S$_2$O$_3$ and stir for 1 hr. Separate the layers and extract the aqueous phase with DCM. Wash the combined organic extracts with saturated aqueous NaHCO$_3$ followed by saturated aqueous NaCl, dry the extracts over anhydrous Na$_2$SO$_4$, filter and concentrate under reduced pressure to give the crude title compound (4.94 g, 85% yield) suitable for use without additional purification. ES/MS (m/z): 243 (M+H).

Preparation 36

4-butyl-1,5,7,8-tetrahydropyrano[3,4-b]pyrazine-2,3-dione

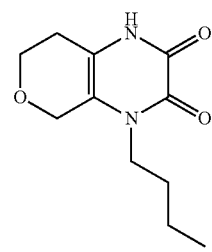 [SMILES: CCCCn1c2c([nH]c(=O)c1=O)CCOC2]

Scheme 3, step C: Dissolve N-butyl-N'-(3-oxotetrahydropyran-4-yl)oxamide (4.9 g, 20.4 mmol) in AcOH (20 mL) and add TFA (1.7 mL, 22 mmol) and TFAA (8.6 mL, 61 mmol). Purge the reaction vessel with N₂ and heat at 75° C. for 7 hr. Add additional TFAA (8.6 mL, 61 mmol) and stir the reaction at 75° C. overnight. Cool to RT and pour onto minimal ice. Add solid NaHCO₃ with stirring to adjust to pH 5-6. Dilute with DCM and the separate the layers. Extract the aqueous layer with DCM, combine the organic extracts, dry over Na₂SO₄, filter, and concentrate under reduced pressure. Dissolve the resulting residue in DCM and filter over a bed of diatomaceous earth, washing with DCM. Additionally extract the aqueous layer with 3:1 CHCl₃/IPA. Combine the organic extracts with with the filtrate, dry over anhydrous Na₂SO₄, filter, and concentrate under reduced pressure to give the crude title compound (3.52 g, 69% yield) suitable for use without additional purification. ES/MS (m/z): 225 (M+H).

Preparation 37

4-butyl-2-chloro-7,8-dihydro-5H-pyrano[3,4-b]pyrazin-3-one

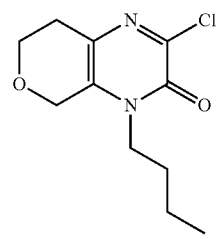 [SMILES: CCCCn1c2c(nc(Cl)c1=O)CCOC2]

Scheme 3, step D: Add 4-butyl-1,5,7,8-tetrahydropyrano[3,4-b]pyrazine-2,3-dione (235 mg, 1.0 mmol) to SOCl₂ (3.5 mL, 48 mmol) and add DMF (0.1 mL, 1 mmol) at RT. Stir the resulting mixture at RT for 2 hr. The reaction is combined with an additional run (35 mg scale reaction) and remove the solvent under reduced pressure, azeotroping with DCM. Dry the resulting residue under vacuum overnight to give the crude title compound (421 mg, 86% yield). Suitable for use without additional purification. ES/MS (m/z): 243(M+H).

Preparation 38

N'-(4-butyl-3-oxo-7,8-dihydro-5H-pyrano[3,4-b]pyrazin-2-yl)-1-cyclopropyl-cyclopropanecarbohydrazide

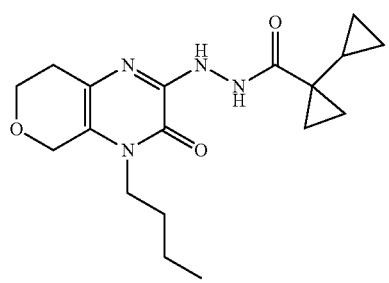 [SMILES: CCCCn1c2c(nc(NNC(=O)C3(C4CC4)CC3)c1=O)CCOC2]

Scheme 3, step G: Irradiate 4-butyl-2-chloro-7,8-dihydro-5H-pyrano[3,4-b]pyrazin-3-one (320 mg, 1.3 mmol) and 1-cyclopropylcyclopropanecarbohydrazide hydrochloride (222 mg, 1.3 mmol) in ACN (4.4 mL) in the microwave at 100° C. for 1 hr. Combine the reaction solution with an additional run (100 mg scale) and quench with water. Partially concentrate the mixture under reduced pressure and extract with EtOAc. Combine the organic extracts, wash with saturated aqueous NaCl, dry over Na₂SO₄, and concentrate under reduced pressure to give the crude title compound (250 mg, 33% yield) suitable for use without additional purification. ES/MS (m/z): 347 (M+H).

Preparation 39

N-(cyclopropylmethyl)-N'-(2-hydroxycycloheptyl)oxamide

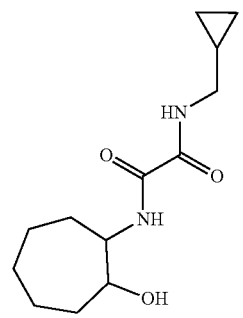 [SMILES: O=C(NCC1CC1)C(=O)NC1CCCCCC1O]

Scheme 4, step B: Add TEA (2.85 mL, 20.4 mmol) to a solution of ethyl 2-(cyclopropylmethylamino)-2-oxoacetate (1.7 g, 10.2 mmol) and 2-aminocycloheptanol (1.5 g, 10.8 mmol) in EtOH (20 mL) and heat at 80° C. for 2 hr. Cool to RT and filter. Wash the filter cake with EtOH and collect as the product. Concentrate the filtrate and purify the resulting residue by flash chromatography on silica, eluting with DCM/MeOH. Combine the pure chromatography fractions with the filter cake and concentrate under reduced pressure to give the title compound as a white solid (1.95 g, 75% yield). ES/MS (m/z): 255.0 (M+H).

Preparation 40

N-(cyclopropylmethyl)-N'-(2-oxocycloheptyl)oxamide

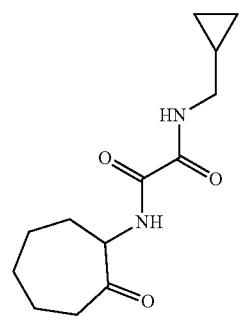 [SMILES: O=C(NCC1CC1)C(=O)NC1CCCCCC1=O]

Scheme 4, step C: Add Dess-Martin periodinane (3.6 g, 8.4 mmol) to a suspension of N-(cyclopropylmethyl)-N'-(2- hydroxycycloheptyl)oxamide (1.95 g, 7.7 mmol) and NaHCO₃ (8.4 g, 99.8 mmol) in DCM (38 mL) and THF (13 mL) at RT. After 2.5 hours, add Na₂S₂O₃ (2.5 g, 15.6 mmol) and water (38 mL) and stir the resulting mixture for an additional 15 minutes. Add additional water and extract with DCM. Wash the combined extracts with saturated aqueous NaCl, dry the extracts over MgSO₄, filter, concentrate under reduced pressure, and purify the resulting residue by flash chromatography on silica gel, eluting with DCM/MTBE. Combine the pure chromatography fractions and concentrate under reduced pressure to obtain the title compound as a white solid (1.7 g, 87% yield). ES/MS (m/z): 253.0 (M+H).

Preparation 41

4-(cyclopropylmethyl)-1,5,6,7,8,9-hexahydrocyclohepta[b]pyrazine-2,3-dione

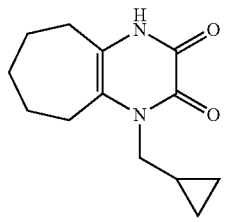 [SMILES: O=c1[nH]c2c(n(CC3CC3)c1=O)CCCCC2]

Scheme 4, step D: Degas a solution of N-(cyclopropylmethyl)-N'-(2-oxocycloheptyl)oxamide (1.7 g, 6.6 mmol) in AcOH (8.3 mL). Add TFA (0.55 mL, 7.3 mmol) and TFAA (1.0 mL, 7.3 mmol), seal the reaction vessel, and heat at 100° C. overnight. Cool to RT, concentrate the reaction mixture under reduced pressure, and purify the resulting residue by flash chromatography on silica, eluting with DCM/MeOH. Combine the pure chromatography fractions and concentrate under reduced pressure to give the title compound as a white solid (1.1 g, 72% yield). ES/MS (m/z): 235.0 (M+H).

Preparation 42

4-(cyclopropylmethyl)-2-hydrazino-6,7,8,9-tetrahydro-5H-cyclohepta[b]pyrazin-3-one

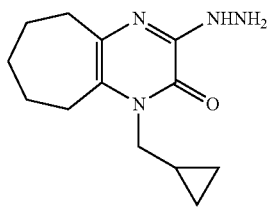 [SMILES: NNc1nc2c(n(CC3CC3)c1=O)CCCCC2]

Scheme 4, step E: Add hydrazine (0.69 mL, 21 mmol) to a suspension of 4-(cyclopropylmethyl)-1,5,6,7,8,9-hexahydrocyclohepta[b]pyrazine-2,3-dione (0.25 g, 1.1 mmol) in EtOH (4.3 mL). Seal the reaction and heat at 100° C. overnight. Cool the reaction to RT, concentrate under reduced pressure, and purify the resulting residue by flash chromatography on silica gel, eluting with DCM/MeOH. Combine the pure chromatography fractions and concentrate under reduced pressure to obtain the title compound as a yellow, sticky film (113 mg, 42% yield). ES/MS (m/z): 249.2 (M+H).

Preparation 43

1-cyclopropyl-N'-[4-(cyclopropylmethyl)-3-oxo-6,7,8,9-tetrahydro-5H-cyclohepta[b]pyrazin-2-yl]cyclopropanecarbohydrazide

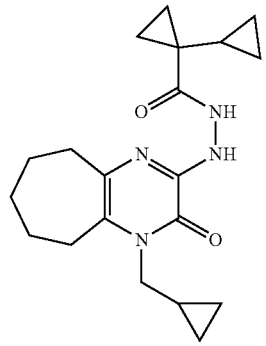 [SMILES: O=C(NNc1nc2c(n(CC3CC3)c1=O)CCCCC2)C1(C2CC2)CC1]

Scheme 4, step F: Add TEA (0.22 mL, 1.6 mmol) to a suspension of 4-(cyclopropylmethyl)-2-hydrazino-6,7,8,9-tetrahydro-5H-cyclohepta[b]pyrazin-3-one (112 mg, 0.4 mmol), 1-cyclopropylcyclopropanecarboxylic acid (68 mg, 0.5 mmol), HOBT (91 mg, 0.7 mmol) and EDCI (137 mg, 0.7 mmol) in THF (4.5 mL) and stir the resulting mixture at RT overnight. Add a small amount of water to the reaction mixture and dilute with EtOAc. Filter the resulting mixture through a bed of diatomaceous earth and wash the filter cake with EtOAc. Concentrate the filtrate and purify by flash chromatography on silica, eluting with DCM/MeOH. Combine the pure chromatography fractions and concentrate under reduced pressure to obtain the title compound as a reddish-brown film (113 mg, 70% yield). ES/MS (m/z): 357.22 (M+H); 355.0 (M−H).

EXAMPLE 1

1-([1,1'-bi(cyclopropan)]-1-yl)-5-propyl-6,7,8,9-tetrahydro-[1,2,4]triazolo[4,3-a]quinoxalin-4(5H)-one

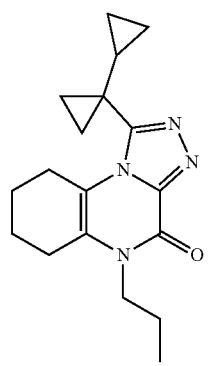

Scheme 1, step J: Wet RaNi (0.1 g) with EtOAc (1 ml) and sparge the slurry with N₂. Add 5-allyl-1-(1-cyclopropylcyclopropyl)-6,7,8,9-tetrahydro-[1,2,4]triazolo[4,3-a]quinoxalin-4-one (201.0 mg, 0.65 mmol) and ethyl acetate (9 ml) to the slurry and shake the mixture under hydrogen (ambient temperature, 60 psi, 1 hour). Filter the mixture and concentrate the filtrate under reduced pressure. Purify the resulting residue by flash chromatography over silica gel, eluting with EtOAc (100%), to give the title compound (116.6 mg, 58%) as a light yellow solid. ES/MS (m/z): 313.2 (M+H).

EXAMPLE 2

1-([1,1'-bi(cyclopropan)]-1-yl)-5-butyl-6,7,8,9-tetrahydro-[1,2,4]triazolo[4,3-a]quinoxalin-4(5H)-one

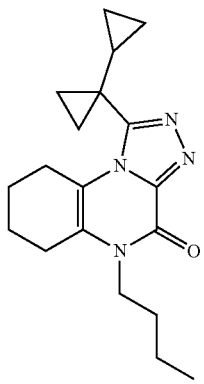 [SMILES: CCCCn1c2c(n3c(C4(C5CC5)CC4)nnc3c1=O)CCCC2]

Scheme 1, step I: Add LHMDS (2.0 g, 2.2 mmol) to a solution of 1-(1-cyclopropylcyclopropyl)-6,7,8,9-tetrahydro-5H-[1,2,4]triazolo[4,3-a]quinoxalin-4-one (202.2 mg, 748.0 μmol) in DMF (5 mL). After stirring the mixture for 1 hour at ambient temperature, add N-butyl iodide (412.9 mg, 2.2 mmol) and stir the mixture at ambient temperature for 2 days. Dilute the mixture with EtOAc and wash with saturated aqueous NaCl. Dry over $Na_2SO_4$, filter, and concentrate under reduced pressure to give a yellow oil. Purify by flash chromatography on silica gel, eluting with EtOAc (100%), to give the title compound (98.2 mg, 40%) as a tan solid. ES/MS (m/z): 327.2 (M+H).

EXAMPLE 3

1-([1,1'-bi(cyclopropan)]-1-yl)-5-(cyclopropylmethyl)-5,6,7,9-tetrahydro-4H-pyrano[4,3-e][1,2,4]triazolo[4,3-a]pyrazin-4-one

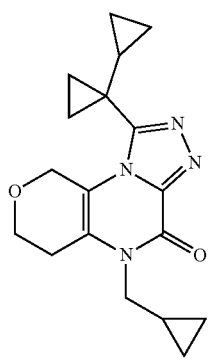 [SMILES: O=c1c2nnc(C3(C4CC4)CC3)n2c2c(n1CC1CC1)CCOC2]

Scheme 2, step F: Combine 1-cyclopropyl-N'-[1-(cyclopropylmethyl)-2-oxo-7,8-dihydro-5H-pyrano[3,4-b]pyrazin-3-yl]cyclopropanecarbohydrazide (344 mg, 0.8 mmol), DBU (38 μL, 0.26 mmol) and HMDS (4 mL) and heat at 120° C. After 7 hr, transfer the reaction mixture to a flask containing MeOH and heat at 50° C. for 1.5 hr. Concentrate under reduced pressure. Purify the resulting residue by flash chromatography on silica gel, eluting with 1:1 EtOAc/DCM to 1:1 EtOAc/(4:1 DCM/MeOH.) Combine the pure chromatography fractions and concentrate under reduced pressure. Combine the impure fractions separately and concentrate under reduced pressure. Dissolve the resulting oil from impure fractions in EtOAc and subject to sonication. Cool the mixture at 0° C. for 1 hr, collect the resulting solids by filtration, and combine with the evaporated pure fractions. Dissolve the solids in ACN/MeOH, evaporate to dryness and additionally dry in vacuum oven overnight to obtain the title compound (155 mg, 58% yield). ES/MS (m/z): 327 (M+H).

EXAMPLE 4

1-([1,1'-bi(cyclopropan)]-1-yl)-5-butyl-5,6,7,9-tetrahydro-4H-pyrano[4,3-e][1,2,4]triazolo[4,3-a]pyrazin-4-one

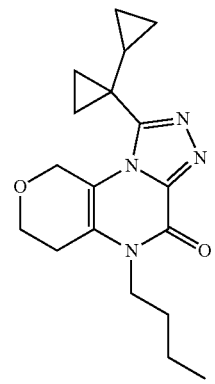 [SMILES: CCCCn1c2c(n3c(C4(C5CC5)CC4)nnc3c1=O)COCC2]

Scheme 2, step F: Combine N'-(1-butyl-2-oxo-7,8-dihydro-5H-pyrano[3,4-b]pyrazin-3-yl)-1-cyclopropyl-cyclopropanecarbohydrazide (832 mg, 1.9 mmol), DBU (58 μL, 0.4 mmol) and HMDS (5 mL) and heat at 120° C. overnight. Transfer to a flask containing MeOH and heat at 50° C. for 1.5 hr. Concentrate under reduced pressure and purify the resulting residue by flash chromatography on silica gel, eluting with 1:1 EtOAc/DCM to 1:1 EtOAc/(90:10 DCM/MeOH). Combine fractions containing product and concentrate under reduced pressure. The resulting residue is purified by reverse phase flash chromatography over C18, eluting with 10-70% ACN in 10% $NaHCO_3$/water. Combine the pure chromatography fractions and concentrate under reduced pressure. Dissolve the resulting residue in MeOH, concentrate under reduced pressure, and dry in vacuum oven for 2 hr to obtain the title compound (265 mg, 42% yield). ES/MS (m/z): 329 (M+H).

EXAMPLE 5

1-([1,1'-bi(cyclopropan)]-1-yl)-5-(cyclobutylmethyl)-5,6,7,9-tetrahydro-4H-pyrano[4,3-e][1,2,4]triazolo[4,3-a]pyrazin-4-one

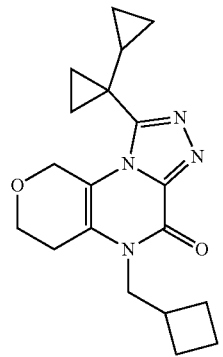 [SMILES: O=c1c2nnc(C3(C4CC4)CC3)n2c2c(n1CC1CCC1)CCOC2]

Scheme 2, step F: Combine N'-[1-(cyclobutylmethyl)-2-oxo-7,8-dihydro-5H-pyrano[3,4-b]pyrazin-3-yl]-1-cyclopropyl-cyclopropanecarbohydrazide (334 mg, 0.8 mmol), DBU (24 µL, 0.16 mmol) and HMDS (2.6 mL) and heat at 120° C. in a microwave vial overnight. Cool to RT and transfer reaction mixture to a flask containing MeOH; heat at 50° C. for 1.5 hr. Concentrate the reaction mixture under reduced pressure and purify the resulting residue by flash chromatography on silica, eluting with 1:1 EtOAc/DCM to 1:1 EtOAc/(90:10 DCM/MeOH). Combine the pure chromatography fractions, concentrate under reduced pressure, and dry under vacuum overnight to obtain the title compound (82 mg, 30% yield). ES/MS (m/z): 341 (M+H).

EXAMPLE 6

1-(1-cyclopropylcyclopropyl)-5-(cyclopropylmethyl)-3-oxo-7,8-dihydro-5H-pyrano-[1,2,4]triazolo[4,3-a]quinoxalin-4-one

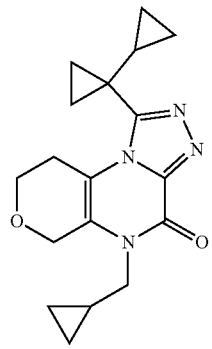 [SMILES: O=c1c2nnc(C3(C4CC4)CC3)n2c2c(n1CC1CC1)COCC2]

Scheme 3, step H: Dissolve 1-cyclopropyl-N'-[4-(cyclopropylmethyl)-3-oxo-7,8-dihydro-5H-pyrano[3,4-b]pyrazin-2-yl]cyclopropanecarbohydrazide (571.7 mg, 1.4 mmol) in AcOH (10 mL), and heat in the microwave for 3 hr at 130° C. Neutralize the reaction mixture with 2N NaOH and extract with EtOAc (3×). Wash the combined organic extracts with saturated aqueous NaCl, dry over $Na_2SO_4$, and concentrate under reduced pressure. Purify the resulting residue by flash chromatography on silica gel, eluting with DCM/EtOAc/MeOH. Combine the pure chromatography fractions and concentrate under reduced pressure to obtain the title compound (119 mg, 23.9% yield). ES/MS (m/z): 327 (M+H).

EXAMPLE 7

1-([1,1'-bi(cyclopropan)]-1-yl)-5-butyl-8,9-dihydro-6H-pyrano[3,4-e][1,2,4]triazolo[4,3-a]pyrazin-4(5H)-one

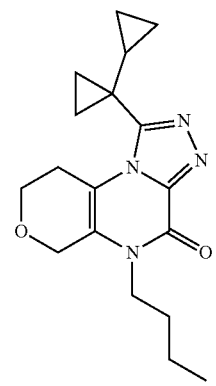 [SMILES: CCCCn1c2c(n3c(C4(C5CC5)CC4)nnc3c1=O)CCOC2]

Scheme 3, step H: Stir a mixture of N'-(4-butyl-3-oxo-7,8-dihydro-5H-pyrano[3,4-b]pyrazin-2-yl)-1-cyclopropyl-cyclopropanecarbohydrazide (250 mg, 0.7 mmol) in HMDS (2.5 mL) at 120° C. overnight. Cool the reaction mixture to RT and stir with methanol at 50° C. for 1 hr. Concentrate the reaction mixture under reduced pressure. Purify the resulting residue by flash chromatography on silica gel, eluting with 0-10% MeOH in DCM to obtain the crude title compound. Further purify the crude title compound by reverse phase flash chromatography on C18, eluting with 10-50% ACN in $H_2O$ to give the title compound (75 mg, 30% yield) after solvent evaporation of the pure fractions. ES/MS (m/z): 329 (M+H).

EXAMPLE 8

1-([1,1'-bi(cyclopropan)]-1-yl)-5-(cyclopropylmethyl)-5,6,7,8,9,10-hexahydro-4H-cyclohepta[e][1,2,4]triazolo[4,3-a]pyrazin-4-one

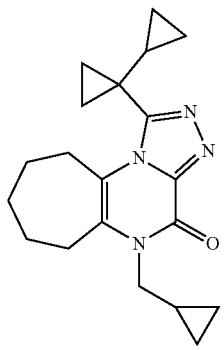 [SMILES: O=c1c2nnc(C3(C4CC4)CC3)n2c2c(n1CC1CC1)CCCCC2]

Scheme 4, step G: Add HMDS (1.0 mL, 4.8 mmol) to a solution of 1-cyclopropyl-N'-[4-(cyclopropylmethyl)-3-oxo-6,7,8,9-tetrahydro-5H-cyclohepta[b]pyrazin-2-yl]cyclopropanecarbohydrazide (0.111 g, 0.311 mmol) in THF (1.0 mL) and heat to 120° C. overnight. Add additional HMDS (2.2 mL, 11 mmol) and continue heating at 120° C. for an additional day. Cool the reaction mixture to RT, slowly add MeOH (1.0 mL), and heat the subsequent mixture at 50° C. for 15 min. Concentrate the mixture under reduced pressure and purify the resulting residue by flash chromatography on silica gel, eluting with DCM/MeOH. Combine the pure chromatography fractions and concentrate under reduced pressure to give the title compound as tan foam (0.04 g, 39% yield). ES/MS (m/z): 339.2 (M+H).

Generation of PDE Proteins

The nucleotide sequences encoding full-length human PDE1A (NP_001003683.1) and PDE1C (NP_005011.1) are inserted into pFastBac1 (Invitrogen) vector with an N-terminal HIS tag. The nucleotide sequences encoding full-length human PDE4D (NP_006194.2) and catalytic domain (residue 641-1141) of PDE3A (NP_000912.3) are inserted into pFastBac1 (Invitrogen) vector with a C-terminal HIS tag. The nucleotide sequences encoding full-length human PDE6A (NP_000431.2) and PDE6B (AAH00249.1) are inserted into pFastBacDual (Invitrogen) vector with an N-terminal HIS tag and N-terminal Flag tag, respectively, for production of PDE6A/6B dimer. Baculovirus generation and protein expression in Sf9 cells are carried out according to the protocol of Bac-to-Bac Baculovirus Expression system (Invitrogen). The nucleotide sequence encoding full-length human PDE1B (NP_000915.1) is inserted into pIEX4 (Novagen) with a C-terminal HIS tag, and both protein productions in Sf9 cells are carried out according to the vendor's protocol (Novagen). The His tagged PDE proteins are purified using Ni-NTA agarose (Qiagen) followed by size exclusion chromatography on a SUPERDEX© 200 column (GE Healthcare) in storage buffer (20 mM Tris-HCl, pH7.5, 150 mM NaCl, 10% Glycerol). The Flag tagged PDE proteins including PDE6A/6B are purified using anti-Flag M2-agarose (Sigma), after purification through NiNTA column chromatography and eluted in storage buffer (50 mM Tris-HCl, pH7.5, 150 mM NaCl, 10% Glycerol, 0.1 mg/ml Flag peptide). All purified proteins are stored at −80° C. in small aliquots.

Phosphodiesterase Enzyme Assays

All 3', 5' cyclic nucleotide phosphodiesterase (PDE) enzyme activities are measured with a radiometric enzyme assay based on SPA detection system (scintillation proximity assay). Compounds to be tested are diluted in pure dimethyl sulfoxide (DMSO) using ten point concentration response curves. Maximal compound concentration in the reaction mixture is either 10 or 100 μM. Compounds at the appropriate concentration are pre-incubated with either of the PDE enzymes for 30 minutes before the reaction is started by the addition of substrate. Reactions are allowed to proceed for 60 minutes at room temperature. Next, reactions are stopped by addition of SPA beads. Samples are read 12 hours later in a MICROBETA™ TRILUX© Counter. "$IC_{50}$" refers to the concentration of the compound that produces 50% of the maximal inhibitory response possible for that compound. $IC_{50}$ values are calculated by plotting the normalized data vs. log [compound] and fitting the data using a four parameter logistic equation.

$Ca^{2+}$ Calmodulin Dependent PDE Enzyme Assays

PDE1B, PDE1A, and PDE1C are cloned and purified following standard protein generation procedures. The assay buffer is prepared to give a final concentration in the assay of 50 mM Tris-HCl, 50 mM $MgC_2$, 4 mM $CaCl_2$, 0.1% Bovine serum albumin and 6 U/ml Calmodulin in water, at pH 7.5. The final enzyme concentration is 0.25, 0.074 and 0.0012 nM, for PDE1A, PDE1B and PDE1C respectively. The reactions are started by addition of the substrate, [$^3$H] cAMP, to give a final concentration of 47 nM.

TABLE 1

In vitro potency of Examples 1 to 8 against human PDE1A, PDE1B, and PDE1C.

| Example | PDE 1A $IC_{50}$ (nM) ± SD (n = number of runs) | PDE 1B $IC_{50}$ (nM) ± SD (n = number of runs) | PDE 1C $IC_{50}$ (nM) ± SD (n = number of runs) |
|---|---|---|---|
| 1 | 2.9 ± 1.9 (n = 4) | 3.1 ± 3.3 (n = 4) | 2.6 ± 3.3 (n = 4) |
| 2 | 3.0 ± 2.1 (n = 6) | 4.1 ± 4.3 (n = 5) | 1.4 ± 0.9 (n = 3) |
| 3 | 9.8 ± 2.2 (n = 3) | 8.7 ± 6.8 (n = 3) | 5.2 ± 0.6 (n = 3) |
| 4 | 6.3 ± 0.4 (n = 2) | 7.8 ± 2.4 (n = 2) | 1.5 ± 0.5 (n = 2) |
| 5 | 5.8 ± 2.3 (n = 2) | 4.2 ± 0 (n = 2) | 1.9 ± 0.4 (n = 2) |
| 6 | 8.4 ± 3.8 (n = 2) | 14.9 ± 5.6 (n = 2) | 7.6 ± 1.9 (n = 2) |
| 7 | 5.2 ± 2.0 (n = 2) | 12.0 ± 2.7 (n = 2) | 2.0 ± 0.1 (n = 2) |
| 8 | 6.5 ± 2.6 (n = 2) | 6.6 ± 2.6 (n = 2) | 4.7 ± 1.4 (n = 2) |

The data in Table 1 demonstrate that the compounds of Examples 1 to 8 inhibit human PDE1A, PDE1B, and PDE1C enzyme activity in vitro.

PDE Enzyme Assays Using [$^3$H]cAMP as Substrate

The following phosphodiesterase activities are measured using [3H]cAMP as reaction substrate: human PDE3A (catalytic domain) and human PDE4D. Both enzymes are cloned and purified following standard procedures. The assay buffer is prepared to give a final concentration in the assay of 50 mM Tris-HCl, 8.3 mM $MgCl_2$, 1.7 mM ethylenediarninetetraacetic acid (EDTA) and 0.1% Bovine serum albumin at pH 7.5. Final enzyme concentrations are 0.008 and 0.021 nM for PDE3A and PDE4D, respectively. Reactions are started by addition of the substrate, [3H]cAMP, to give a final concentration of 47 nM.

TABLE 2

In vitro potency of Examples 1 to 8 against human PDE3A (catalytic domain) and PDE4D.

| Example | PDE 3A $IC_{50}$ (μm) ± SD (n = number of runs) | PDE 4D $IC_{50}$ (μm) ± SD (n = number of runs) |
|---|---|---|
| 1 | >100 (n = 1) | 12.7 (n = 1) |
| 2 | >100 (n = 1) | 13.2 ± 2.5 (n = 4) |
| 3 | >100 (n = 1) | 16.4 ± 0.3 (n = 3) |
| 4 | >100 (n = 1) | 21.8 (n = 1) |
| 5 | >100 (n = 1) | 19.2 (n = 1) |
| 6 | >100 (n = 1) | 39.2 ± 16.5 (n = 2) |
| 7 | >100 (n = 1) | >100 (n = 1) |
| 8 | >100 (n = 1) | 12.1 (n = 1) |

PDE Enzyme Assays Using [³H]cGMP as Substrate

The following phosphodiesterase activities are measured using [3H]cGMP as reaction substrate: human PDE6A/6B. The catalytic active form of human PDE6 is a dimer composed of a α (human PDE6A) and β subunit (human PDE6B). The dimer of human PDE6A/6B is produced by the expression and purification strategy, using two purification steps, i.e., NiNTA and anti-FLAG Sepharose chromatography. The assay buffer is prepared to give a final concentration in the assay of 50 mM Tris-HCl, 8.3 mM $MgC_2$, 1.7 mM EDTA and 0.1% Bovine serum albumin at pH 7.5. The final enzyme concentration is 5 nM. The reactions are started by addition of the substrate, [3H]cGMP, to give a final concentration of 80 nM.

TABLE 3

In vitro potency of Example 1 to 8 against PDE6AB.

| Example | PDE 6AB $IC_{50}$ (μM) ± SD (n = number of runs) |
|---|---|
| 1 | >10 (n = 1) |
| 2 | >10 (n = 1) |
| 3 | >10 (n = 1) |
| 4 | >10 (n = 1) |
| 5 | >10 (n = 1) |
| 6 | >10 (n = 1) |
| 7 | >10 (n = 1) |
| 8 | >10 (n = 1) |

The data in Tables 1, 2, and 3 demonstrate that the compounds of Examples 1 to 8 are selective inhibitors of human PDE1A, PDE1B, and PDE1C relative to human PDE3A, PDE4D, and PDE6AB in vitro.

We claim:

1. A compound of the formula:

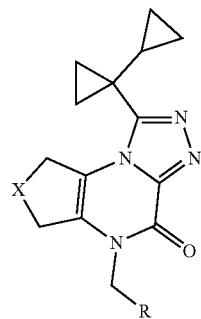

wherein X is $CH_2CH_2$, $CH_2CH_2CH_2$, $OCH_2$, or $CH_2O$; and R is ethyl, n-propyl, cyclopropyl, or cyclobutyl; or a pharmaceutically acceptable salt thereof; with the proviso that when X is $CH_2CH_2$, then R is other than cyclopropyl.

2. The compound or salt according to claim 1 wherein X is $OCH_2$.

3. The compound or salt according to claim 1 wherein X is $CH_2O$.

4. The compound or salt according to claim 1 wherein R is cyclopropyl.

5. The compound or salt according to claim 1 wherein R is n-propyl.

6. The compound or salt according to claim 1 which is:

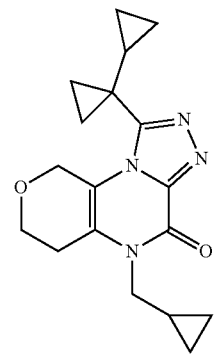

7. The compound according to claim 6 which is:

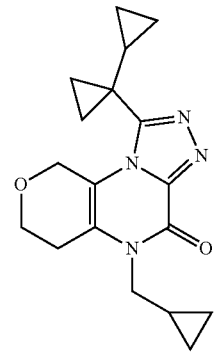

8. The compound or salt according to claim 1 which is:

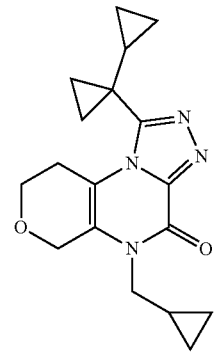

9. The compound according to claim 8 which is:

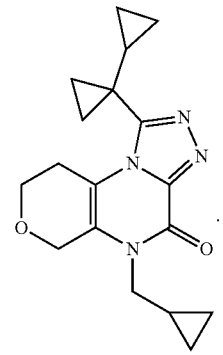 [SMILES: O=c1c2nnc(C3(C4CC4)CC3)n2c2c(n1CC1CC1)COCC2]

10. A method of restraining, slowing, or reversing the progression or severity of an existing symptom of chronic kidney disease, comprising administering to a patient in need thereof an effective amount of a compound according to claim 1, or a pharmaceutically-acceptable salt thereof.

11. A method of restraining, slowing, or reversing the progression or severity of an existing symptom of diabetic kidney disease, comprising administering to a patient in need thereof an effective amount of a compound according to claim 1, or a pharmaceutically-acceptable salt thereof.

12. A pharmaceutical composition, comprising a compound or a pharmaceutically-acceptable salt thereof according to claim 1, with one or more pharmaceutically acceptable carriers, diluents, or excipients.

13. A process for preparing a pharmaceutical composition, comprising admixing a compound according to claim 1, or a pharmaceutically-acceptable salt thereof, with one or more pharmaceutically acceptable carriers, diluents, or excipients.

\* \* \* \* \*